United States Patent
Yokoi et al.

(10) Patent No.: US 10,323,251 B2
(45) Date of Patent: Jun. 18, 2019

(54) METHOD UTILIZING PIGGYBAC TRANSPOSON AND TRANSPOSASE TO INTRODUCE MUTATION INTO TARGET DNA IN A PLANT CELL

(71) Applicant: NATIONAL RESEARCH AND DEVELOPMENT AGENCY NATIONAL AGRICULTURE AND FOOD RESEARCH ORGANIZATION, Tsukuba-shi, Ibaraki (JP)

(72) Inventors: Ayako Yokoi, Tsukuba (JP); Seiichi Toki, Tsukuba (JP)

(73) Assignee: NATIONAL RESEARCH AND DEVELOPMENT AGENCY NATIONAL AGRICULTURE AND FOOD RESEARCH ORGANIZATION, Tsukuba-shi, Ibaraki (JP)

( * ) Notice: Subject to any disclaimer, the term of this patent is extended or adjusted under 35 U.S.C. 154(b) by 0 days.

(21) Appl. No.: 15/119,425

(22) PCT Filed: Feb. 19, 2015

(86) PCT No.: PCT/JP2015/054610
§ 371 (c)(1),
(2) Date: Aug. 17, 2016

(87) PCT Pub. No.: WO2015/125862
PCT Pub. Date: Aug. 27, 2015

(65) Prior Publication Data
US 2017/0058285 A1    Mar. 2, 2017

(30) Foreign Application Priority Data

Feb. 19, 2014   (JP) .................. 2014-029587

(51) Int. Cl.
C12N 15/82        (2006.01)
(52) U.S. Cl.
CPC ..... *C12N 15/8213* (2013.01); *C12N 15/8209* (2013.01); *C12N 15/8216* (2013.01)
(58) Field of Classification Search
None
See application file for complete search history.

(56) References Cited

U.S. PATENT DOCUMENTS

| | | | | |
|---|---|---|---|---|
| 5,527,695 A | * | 6/1996 | Hodges | C12N 15/8213 800/291 |
| 2007/0016980 A1 | * | 1/2007 | Lyznik | C12N 9/00 800/280 |

FOREIGN PATENT DOCUMENTS

| | | |
|---|---|---|
| JP | 2005-519631 A | 7/2005 |
| JP | 2013-514764 A | 5/2013 |
| JP | 2013-529915 A | 7/2013 |
| WO | 03/087341 A2 | 10/2003 |
| WO | 2011/078665 A1 | 6/2011 |
| WO | 2011/154393 A1 | 12/2011 |

OTHER PUBLICATIONS

Nishizawa-Yokoi et al. The development of targeted genome engineering in plants. (2013) Regulation of Plant Growth & Development; vol. 48; pp. 117-124.*
Lee et al. Homologous recombination in plant cells after Agrobacterium-mediated transformation. (1990) The Plant Cell; vol. 2, pp. 415-425).*
Puchta, H. Towards the ideal GMP: homologous recombination and marker gene excision. (2003) J. Plant Physiol.; vol. 160; pp. 743-754.*
Masson et al. Mobility of the maize suppressor-mutator element in transgenic tobacco cells. (1989) PNAS; vol. 86; pp. 2219-2223.*
Terada et al. Gene targeting by homologous recombination as a biotechnological tool for rice functional genomics. (2007) Plant Physiology; vol. 144; pp. 846-856 (Year: 2007).*
Nishizawa-Yokoi, Ayako et al., "The development of targeted genome engineering in plants", Regulation of Plant Growth & Development, Dec. 20, 2013, vol. 48, No. 2, pp. 117-124 (total 9 pages).
Endo, Masaki et al., "Shokubutsu Genome no Hyoteki Idenshi Kaihen ni Okeru Jinko Seigen Koso no Riyo", Biotechnology (Seibutsu-kogaku Kaisha), Aug. 25, 2013, vol. 91, No. 8, pp. 348-351 (total 5 pages).
Endo, Masaki et al., "Toward establishing an efficient and versatile gene targeting system in higher plants", Biocatalysis and Agricultural Biotechnology, Oct. 11, 2013, vol. 3, pp. 2-6.
Nishizawa-Yokoi, Ayako et al., "Precise marker excision system using an animal-derived piggyBac transposon in plants", The Plant Journal, Oct. 26, 2013, vol. 77, pp. 454-463.
Yokoi, Ayako et al., "PiggyBac Transposon o Mochiita Sokuseki o Nokosanai Senbatsu Marker Idenshi Jokyo-kei no Kaihatsu", Dai 31 kai Japanese Society for Plant Cell and Molecular Biology (Sapporo) Taikai Symposium Koen Yoshishu, Sep. 10, 2013, 1Ca-08, pp. 142 (total 11 pages).

(Continued)

*Primary Examiner* — Cathy Kingdon Worley
(74) *Attorney, Agent, or Firm* — Sughrue Mion, PLLC

(57) ABSTRACT

A method for producing a plant cell comprising a mutation introduced in a target DNA comprises:
a step of introducing into plant cells a DNA construct comprising a DNA homologous to a target DNA, wherein a desired mutation is introduced and a piggyBac transposon containing a marker gene is inserted in the homologous DNA;
a step of selecting a plant cell, in which the mutation and the piggyBac transposon are introduced in the target DNA via homologous recombination, based on an expression of the marker gene; and
a step of removing the piggyBac transposon from the target DNA by constitutively expressing a piggyBac transposase in the cell selected in the above step.

2 Claims, 9 Drawing Sheets

Specification includes a Sequence Listing.

(56) References Cited

OTHER PUBLICATIONS

Nishizawa-Yokoi, Ayako et al., "Precision genome editing in plants via gene targeting and piggyBac-mediated marker excision", The Plant Journal, Oct. 6, 2014, vol. 81, pp. 160-168.
Yusa, Kosuke et al., "Targeted gene correction of $\alpha_1$-antitrypsin deficiency in induced pluripotent stem cells", Nature, Apr. 20, 2012, vol. 478, Issue 7369, pp. 391-394 (total 15 pages).
Nishizawa-Yokoi, Ayako et al., "Precise marker excision system in plants", Proceeding of the 54th Annual Meeting of The Japanese Society of Plant Physiologists, Mar. 14, 2013, PF250 (0725), pp. 297 (total 7 pages). Translation.
Nishizawa-Yokoi, Ayako et al., "Precision genome engineering in rice", Proceeding of Keystone Symposia on Molecular and Cellular Biology, Mar. 2013, 2027, pp. 63 (total 3 pages).
Yokoi, Ayako et al., "Development of Marker Gene Removal System using Transposon without Leaving Footprint in Plants", Breeding Research, Mar. 27 and 28, 2013, vol. 15, Sup. 1, pp. 172 (total 13 pages).
Saika, Hiroaki et al., "Development and Application of New Genome Modification Technique in Plants", Bioscience and Industry, 2013, vol. 71, No. 3, pp. 275-278 (total 18 pages).
International Search Report dated May 19, 2015, issued by the International Searching Authority in application No. PCT/JP2015/054610.
International Preliminary Report on Patentability with translation of Written Opinion dated Sep. 1, 2016, issued by the International Searching Authority in application No. PCT/JP2015/054610.
Dang et al., "Gene Editing a Constitutively Active OsRac1 by Homologous Recombination-Based Gene Targeting Induces Immune Responses in Rice," Plant Cell Physiology, 2013, 54(12): 2058-2070.
Iida et al., "Modification of endogenous natural genes by gene targeting in rice and other higher plants", Plant Molecular Biology, 2005 vol. 59, pp. 205-219.
Fauser et al., "In planta gene targeting", PNAS, May 8, 2012, vol. 109, No. 19, pp. 7535-7540.
Communication dated Sep. 28, 2018 from the Japanese Patent Office in counterpart application No. 2015-030734.

* cited by examiner

```
SEQUENCE LISTING

<160> NUMBER OF SEQ ID NOS: 42

<210> SEQ ID NO 1
<211> LENGTH: 13
<212> TYPE: DNA
<213> ORGANISM: Artificial Sequence
<220> FEATURE:
<223> OTHER INFORMATION: inverted repeat

<400> SEQUENCE: 1
ccctagaaag ata                                                          13

<210> SEQ ID NO 2
<211> LENGTH: 35
<212> TYPE: DNA
<213> ORGANISM: Artificial Sequence
<220> FEATURE:
<223> OTHER INFORMATION: inverted repeat

<400> SEQUENCE: 2
ccctagaaag atagtctgcg taaaattgac gcatg                                  35

<210> SEQ ID NO 3
<211> LENGTH: 63
<212> TYPE: DNA
<213> ORGANISM: Artificial Sequence
<220> FEATURE:
<223> OTHER INFORMATION: inverted repeat

<400> SEQUENCE: 3
ccctagaaag ataatcatat tgtgacgtac gttaaagata atcatgcgta aaattgacgc        60
atg                                                                     63

<210> SEQ ID NO 4
<211> LENGTH: 63
<212> TYPE: DNA
<213> ORGANISM: Artificial Sequence
<220> FEATURE:
<223> OTHER INFORMATION: inverted repeat

<400> SEQUENCE: 4
catgcgtcaa ttttacgcat gattatcttt aacgtacgtc acaatatgat tatctttcta        60
ggg                                                                     63

<210> SEQ ID NO 5
<211> LENGTH: 35
<212> TYPE: DNA
<213> ORGANISM: Artificial Sequence
<220> FEATURE:
<223> OTHER INFORMATION: inverted repeat
```

<400> SEQUENCE: 5

```
catgcgtcaa ttttacgcag actatctttc taggg                                35
```

<210> SEQ ID NO 6
<211> LENGTH: 1785
<212> TYPE: DNA
<213> ORGANISM: Artificial Sequence
<220> FEATURE:
<221> NAME/KEY: CDS
<222> LOCATION: (1)..(1785)
<223> OTHER INFORMATION: hyperactive piggyBac transposase

<400> SEQUENCE: 6

```
atg ggc agc agc ctg gac gac gag cac atc ctg agc gcc ctg ctg cag      48
Met Gly Ser Ser Leu Asp Asp Glu His Ile Leu Ser Ala Leu Leu Gln
 1               5                  10                  15 agc gac gac gag ctg gtc ggc gag gac agc gac agc gag gtg agc gac      96
Ser Asp Asp Glu Leu Val Gly Glu Asp Ser Asp Ser Glu Val Ser Asp
             20                  25                  30 cac gtg agc gag gac gac gtg cag tcc gac acc gag gag gcc ttc atc     144
His Val Ser Glu Asp Asp Val Gln Ser Asp Thr Glu Glu Ala Phe Ile
         35                  40                  45 gac gag gtg cac gag gtg cag cct acc agc agc ggc tcc gag atc ctg     192
Asp Glu Val His Glu Val Gln Pro Thr Ser Ser Gly Ser Glu Ile Leu
     50                  55                  60 gac gag cag aac gtg atc gag cag ccc ggc agc tcc ctg gcc agc aac     240
Asp Glu Gln Asn Val Ile Glu Gln Pro Gly Ser Ser Leu Ala Ser Asn
 65                  70                  75                  80 agg atc ctg acc ctg ccc cag agg acc atc agg ggc aag aac aag cac     288
Arg Ile Leu Thr Leu Pro Gln Arg Thr Ile Arg Gly Lys Asn Lys His
                 85                  90                  95 tgc tgg tcc acc tcc aag ccc acc agg cgg agc agg gtg tcc gcc ctg     336
Cys Trp Ser Thr Ser Lys Pro Thr Arg Arg Ser Arg Val Ser Ala Leu
            100                 105                 110 aac atc gtg aga agc cag agg ggc ccc acc agg atg tgc agg aac atc     384
Asn Ile Val Arg Ser Gln Arg Gly Pro Thr Arg Met Cys Arg Asn Ile
        115                 120                 125 tac gac ccc ctg ctg tgc ttc aag ctg ttc ttc acc gac gag atc atc     432
Tyr Asp Pro Leu Leu Cys Phe Lys Leu Phe Phe Thr Asp Glu Ile Ile
    130                 135                 140 agc gag atc gtg aag tgg acc aac gcc gag atc agc ctg aag agg cgg     480
Ser Glu Ile Val Lys Trp Thr Asn Ala Glu Ile Ser Leu Lys Arg Arg
145                 150                 155                 160 gag agc atg acc tcc gcc acc ttc agg gac acc aac gag gac gag atc     528
Glu Ser Met Thr Ser Ala Thr Phe Arg Asp Thr Asn Glu Asp Glu Ile
                165                 170                 175 tac gcc ttc ttc ggc atc ctg gtg atg acc gcc gtg agg aag gac aac     576
Tyr Ala Phe Phe Gly Ile Leu Val Met Thr Ala Val Arg Lys Asp Asn
            180                 185                 190 cac atg agc acc gac gac ctg ttc gac aga tcc ctg agc atg gtg tac     624
His Met Ser Thr Asp Asp Leu Phe Asp Arg Ser Leu Ser Met Val Tyr
        195                 200                 205 gtg agc gtg atg agc agg gac aga ttc gac ttc ctg atc aga tgc ctg     672
Val Ser Val Met Ser Arg Asp Arg Phe Asp Phe Leu Ile Arg Cys Leu
    210                 215                 220 agg atg gac gac aag agc atc agg ccc acc ctg cgg gag aac gac gtg     720
Arg Met Asp Asp Lys Ser Ile Arg Pro Thr Leu Arg Glu Asn Asp Val
225                 230                 235                 240 ttc acc ccc gtg aga aag atc tgg gac ctg ttc atc cac cag tgc atc     768
Phe Thr Pro Val Arg Lys Ile Trp Asp Leu Phe Ile His Gln Cys Ile
                245                 250                 255
```

| | | |
|---|---|---|
| cag aac tac acc cct ggc gcc cac ctg acc atc gac gag cag ctg ctg<br>Gln Asn Tyr Thr Pro Gly Ala His Leu Thr Ile Asp Glu Gln Leu Leu<br>260 265 270 | 816 |
| ggc ttc agg ggc agg tgc ccc ttc agg gtc tat atc ccc aac aag ccc<br>Gly Phe Arg Gly Arg Cys Pro Phe Arg Val Tyr Ile Pro Asn Lys Pro<br>275 280 285 | 864 |
| agc aag tac ggc atc aag atc ctg atg atg tgc gac agc ggc acc aag<br>Ser Lys Tyr Gly Ile Lys Ile Leu Met Met Cys Asp Ser Gly Thr Lys<br>290 295 300 | 912 |
| tac atg atc aac ggc atg ccc tac ctg ggc agg ggc acc cag acc aac<br>Tyr Met Ile Asn Gly Met Pro Tyr Leu Gly Arg Gly Thr Gln Thr Asn<br>305 310 315 320 | 960 |
| ggc gtg ccc ctg ggc gag tac tac gtg aag gag ctg tcc aag ccc gtc<br>Gly Val Pro Leu Gly Glu Tyr Tyr Val Lys Glu Leu Ser Lys Pro Val<br>325 330 335 | 1008 |
| cac ggc agc tgc aga aac atc acc tgc gac aac tgg ttc acc agc atc<br>His Gly Ser Cys Arg Asn Ile Thr Cys Asp Asn Trp Phe Thr Ser Ile<br>340 345 350 | 1056 |
| ccc ctg gcc aag aac ctg ctg cag gag ccc tac aag ctg acc atc gtg<br>Pro Leu Ala Lys Asn Leu Leu Gln Glu Pro Tyr Lys Leu Thr Ile Val<br>355 360 365 | 1104 |
| ggc acc gtg aga agc aac aag aga gag atc ccc gag gtc ctg aag aac<br>Gly Thr Val Arg Ser Asn Lys Arg Glu Ile Pro Glu Val Leu Lys Asn<br>370 375 380 | 1152 |
| agc agg tcc agg ccc gtg ggc acc agc atg ttc tgc ttc gac ggc ccc<br>Ser Arg Ser Arg Pro Val Gly Thr Ser Met Phe Cys Phe Asp Gly Pro<br>385 390 395 400 | 1200 |
| ctg acc ctg gtg tcc tac aag ccc aag ccc gcc aag atg gtg tac ctg<br>Leu Thr Leu Val Ser Tyr Lys Pro Lys Pro Ala Lys Met Val Tyr Leu<br>405 410 415 | 1248 |
| ctg tcc agc tgc gac gag gac gcc agc atc aac gag agc acc ggc aag<br>Leu Ser Ser Cys Asp Glu Asp Ala Ser Ile Asn Glu Ser Thr Gly Lys<br>420 425 430 | 1296 |
| ccc cag atg gtg atg tac tac aac cag acc aag ggc ggc gtg gac acc<br>Pro Gln Met Val Met Tyr Tyr Asn Gln Thr Lys Gly Gly Val Asp Thr<br>435 440 445 | 1344 |
| ctg gac cag atg tgc agc gtg atg acc tgc agc aga aag acc aac agg<br>Leu Asp Gln Met Cys Ser Val Met Thr Cys Ser Arg Lys Thr Asn Arg<br>450 455 460 | 1392 |
| tgg ccc atg gcc ctg ctg tac ggc atg atc aac atc gcc tgc atc aac<br>Trp Pro Met Ala Leu Leu Tyr Gly Met Ile Asn Ile Ala Cys Ile Asn<br>465 470 475 480 | 1440 |
| agc ttc atc atc tac agc cac aac gtg agc agc aag ggc gag aag gtg<br>Ser Phe Ile Ile Tyr Ser His Asn Val Ser Ser Lys Gly Glu Lys Val<br>485 490 495 | 1488 |
| cag agc cgg aaa aag ttc atg cgg aac ctg tac atg ggc ctg acc tcc<br>Gln Ser Arg Lys Lys Phe Met Arg Asn Leu Tyr Met Gly Leu Thr Ser<br>500 505 510 | 1536 |
| agc ttc atg agg aag agg ctg gag gcc ccc acc ctg aag aga tac ctg<br>Ser Phe Met Arg Lys Arg Leu Glu Ala Pro Thr Leu Lys Arg Tyr Leu<br>515 520 525 | 1584 |
| agg gac aac atc agc aac atc ctg ccc aaa gag gtg ccc ggc acc agc<br>Arg Asp Asn Ile Ser Asn Ile Leu Pro Lys Glu Val Pro Gly Thr Ser<br>530 535 540 | 1632 |
| gac gac agc acc gag gag ccc gtg atg aag aag agg acc tac tgc acc<br>Asp Asp Ser Thr Glu Glu Pro Val Met Lys Lys Arg Thr Tyr Cys Thr<br>545 550 555 560 | 1680 |
| tac tgt ccc agc aag atc aga aga aag gcc agc gcc agc tgc aag aag<br>Tyr Cys Pro Ser Lys Ile Arg Arg Lys Ala Ser Ala Ser Cys Lys Lys | 1728 |

```
                         565                 570                 575
tgt aag aag gtc atc tgc cgg gag cac aac atc gac atg tgc cag agc      1776
Cys Lys Lys Val Ile Cys Arg Glu His Asn Ile Asp Met Cys Gln Ser
        580                 585                 590 tgt ttc tga                                                          1785
Cys Phe <210> SEQ ID NO 7
<211> LENGTH: 594
<212> TYPE: PRT
<213> ORGANISM: Artificial Sequence
<220> FEATURE:
<223> OTHER INFORMATION: hyperactive piggyBac transposase

<400> SEQUENCE: 7

Met Gly Ser Ser Leu Asp Asp Glu His Ile Leu Ser Ala Leu Leu Gln
1               5                  10                  15

Ser Asp Asp Glu Leu Val Gly Glu Asp Ser Asp Ser Glu Val Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Pro Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Ser Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Val Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320
```

```
Gly Val Pro Leu Gly Glu Tyr Tyr Val Lys Glu Leu Ser Lys Pro Val
            325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
            355                 360                 365

Gly Thr Val Arg Ser Asn Lys Arg Glu Ile Pro Glu Val Leu Lys Asn
370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
            405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
            450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
            485                 490                 495

Gln Ser Arg Lys Lys Phe Met Arg Asn Leu Tyr Met Gly Leu Thr Ser
            500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Lys Glu Val Pro Gly Thr Ser
530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Ser Ala Ser Cys Lys Lys
            565                 570                 575

Cys Lys Lys Val Ile Cys Arg Glu His Asn Ile Asp Met Cys Gln Ser
            580                 585                 590

Cys Phe

<210> SEQ ID NO 8
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 8
tgctggatga gttaacgaaa ggtgagg                                    27

<210> SEQ ID NO 9
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 9
cctcaccttt cgttaactca tccagca                                    27

<210> SEQ ID NO 10
```

```
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 10
gacatgacaa ccagtcatcc gattaggttt                                          30

<210> SEQ ID NO 11
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 11
ctgacgatga gaatatatct gatgctgtga                                          30

<210> SEQ ID NO 12
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 12
acatacccat ccaacaatgt tcaatccctt                                          30

<210> SEQ ID NO 13
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 13
tctggagata gcatacttgc tttgcttggt                                          30

<210> SEQ ID NO 14
<211> LENGTH: 17
<212> TYPE: DNA
<213> ORGANISM: Artificial Sequence
<220> FEATURE:
<223> OTHER INFORMATION: Artificially synthesized primer sequence

<400> SEQUENCE: 14
caggaaacag ctatgac                                                        17

<210> SEQ ID NO 15
<211> LENGTH: 17
<212> TYPE: DNA
<213> ORGANISM: Artificial Sequence
<220> FEATURE:
<223> OTHER INFORMATION: Artificially synthesized primer sequence

<400> SEQUENCE: 15
gtaaaacgac ggccagt                                                        17

<210> SEQ ID NO 16
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 16
```
acttgggatc ataggcagca                                              20

<210> SEQ ID NO 17
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 17
ccttagcagt caggaatagc ttg                                          23

<210> SEQ ID NO 18
<211> LENGTH: 29
<212> TYPE: DNA
<213> ORGANISM: Artificial Sequence
<220> FEATURE:
<223> OTHER INFORMATION: Artificially synthesized primer sequence

<400> SEQUENCE: 18
caaagatcgt tatgtttatc ggcactttg                                    29

<210> SEQ ID NO 19
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 19
ctcgagctat ttctttgccc tc                                           22

<210> SEQ ID NO 20
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 20
gtacgcaaat tatgccgtgg a                                            21

<210> SEQ ID NO 21
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 21 ttcttttca atactttcct cgcttgctct                                    30

<210> SEQ ID NO 22
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 22
attcagccac ttatcttgac acaaccattt                                   30

<210> SEQ ID NO 23
<211> LENGTH: 20
<212> TYPE: DNA

```
<213> ORGANISM: Artificial Sequence
<220> FEATURE:
<223> OTHER INFORMATION: Artificially synthesized primer sequence

<400> SEQUENCE: 23
tgtgacagcc cagtcatcat                                              20

<210> SEQ ID NO 24
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 24
cgttggatcg acatcatcag                                              20

<210> SEQ ID NO 25
<211> LENGTH: 29
<212> TYPE: DNA
<213> ORGANISM: Artificial Sequence
<220> FEATURE:
<223> OTHER INFORMATION: Artificially synthesized primer sequence

<400> SEQUENCE: 25
caaagatcgt tatgtttatc ggcactttg                                    29

<210> SEQ ID NO 26
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 26
ctcgagctat ttctttgccc tc                                           22

<210> SEQ ID NO 27
<211> LENGTH: 21
<212> TYPE: DNA
<213> ORGANISM: Oryza sativa
<220> FEATURE:
<221> NAME/KEY: misc_feature
<222> LOCATION: (1)..(21)
<223> OTHER INFORMATION: micro RNA targeting site

<400> SEQUENCE: 27
cagcagcatc atcacgattc c                                            21

<210> SEQ ID NO 28
<211> LENGTH: 21
<212> TYPE: DNA
<213> ORGANISM: Oryza sativa
<220> FEATURE:
<221> NAME/KEY: misc_feature
<222> LOCATION: (1)..(21)
<223> OTHER INFORMATION: micro RNA targeting site

<400> SEQUENCE: 28
cagcagcgtc atcacgattc c                                            21

<210> SEQ ID NO 29
<211> LENGTH: 30
<212> TYPE: DNA
<213> ORGANISM: Artificial Sequence
<220> FEATURE:
<223> OTHER INFORMATION: Artificially synthesized primer sequence
```

```
<400> SEQUENCE: 29
ttggcgcgcc ttgtcgtcac gcgccagttc                                     30

<210> SEQ ID NO 30
<211> LENGTH: 35
<212> TYPE: DNA
<213> ORGANISM: Artificial Sequence
<220> FEATURE:
<223> OTHER INFORMATION: Artificially synthesized primer sequence

<400> SEQUENCE: 30
ccttaattaa tccagggaaa tccaccacta ctact                               35

<210> SEQ ID NO 31
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 31
tcggtcggct aaggtttgct actaaaaaca                                     30

<210> SEQ ID NO 32
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 32
cttgcacgac ggttctacag gagattagtg                                     30

<210> SEQ ID NO 33
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 33
cgaccagaac tcgaaccatc                                                20

<210> SEQ ID NO 34
<211> LENGTH: 28
<212> TYPE: DNA
<213> ORGANISM: Artificial Sequence
<220> FEATURE:
<223> OTHER INFORMATION: Artificially synthesized primer sequence

<400> SEQUENCE: 34
ggatgctatt cttttgctct accttttt                                       28

<210> SEQ ID NO 35
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 35
ttactttagt accaacatct agaaggacga                                     30

<210> SEQ ID NO 36
```

```
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 36
ctattccctg ctcgcccaat                                              20

<210> SEQ ID NO 37
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 37
agactgaaaa cggccaatgc                                              20

<210> SEQ ID NO 38
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 38
cttcgagatg ttagatatgt gtgc                                         24

<210> SEQ ID NO 39
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 39
ggttccattc cctgacccgg cccacct                                      27

<210> SEQ ID NO 40
<211> LENGTH: 29
<212> TYPE: DNA
<213> ORGANISM: Artificial Sequence
<220> FEATURE:
<223> OTHER INFORMATION: Artificially synthesized primer sequence

<400> SEQUENCE: 40
cagtgaatga tgcaacatga gaccgaaca                                    29

<210> SEQ ID NO 41
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 41
cagtcatctg gacttgttgg aattg                                        25

<210> SEQ ID NO 42
<211> LENGTH: 24
<212> TYPE: DNA
<213> ORGANISM: Artificial Sequence
<220> FEATURE:
<223> OTHER INFORMATION: Artificially synthesized primer sequence
```

-continued

```
<400> SEQUENCE: 42
catcggatga gaccacatta actt                                          24
```

METHOD UTILIZING PIGGYBAC TRANSPOSON AND TRANSPOSASE TO INTRODUCE MUTATION INTO TARGET DNA IN A PLANT CELL

CROSS REFERENCE TO RELATED APPLICATIONS

This application is a National Stage of International Application No. PCT/JP2015/054610 filed Feb. 19, 2015, claiming priority based on Japanese Patent Application No. 2014-029587 filed Feb. 19, 2014, the contents of all of which are incorporated herein by reference in their entirety.

TECHNICAL FIELD

The present invention relates to a plant cell comprising a mutation introduced in a target DNA, and a plant comprising the plant cell, as well as a progeny, a clone, and a propagation material of the plant. Moreover, the present invention relates to a method for producing the plant cell, a DNA construct for use in the production method, and a kit comprising the DNA construct.

BACKGROUND ART

Gene targeting (GT) is a technique of modifying a target DNA on a genome at will by recombination utilizing the base sequence homology of DNAs. In the field of plants also, this technique is very promising in the fundamental research and in the development of breeding materials.

Nevertheless, the frequency of the homologous recombination in higher plants is low. When vector shaving a certain mutation on a sequence homologous to a target DNA (GT vectors) are introduced into cells from the outside to modify the target DNA via GT, most of the vectors are randomly inserted into the genomes. Against this background, positive-negative selection has been developed to efficiently select cells in which GT has successfully occurred. This method is a selection method in which cells having GT vectors randomly incorporated in the genomes are eliminated on the basis of the expression of a negative selectable marker gene, while cells having mutations introduced in target DNAs by GT are isolated on the basis of the expression of a positive selectable marker gene.

However, when this method is used, the expression cassette of the positive selectable marker gene remains in the target DNA. Accordingly, this cassette needs to be removed in a case where only a required mutation is to be introduced into a target DNA. In this regard, there has been a report so far on a system in which a positive selectable marker gene is removed after GT using a site-specific recombinase. Nevertheless, when this system is used, the recognition sequence of the site-specific recombinase remains after the marker is removed. Since it is also reported that even inserting a short base sequence influences the expressions of adjacent genes, there has been a demand for the development of a technique capable of marker removal without leaving any footprint after GT, and used when an introduction system is constructed for a mutation equivalent to a spontaneous mutation.

Regarding such a technique, there has been a report that only a required mutation was successfully introduced into a target DNA in mammalian cells by utilizing a special transposon, piggyBac transposon (hereinafter also referred to as "piggyBac"), which leaves no footprint after the transposition (NPL 1). To be more specific, it has been revealed that, after the modification of target DNAs by GT, transiently expressing a piggyBac transposase (hereinafter also referred to as "transposase") in mouse- and human-derived culture cells made is possible to remove positive selectable marker genes from the target DNAs.

Nevertheless, in such a mutation introduction system for mammalian cells, the efficiency of removing piggyBac and positive selectable marker genes is so low that a negative selection needs to be performed to obtain cells from which piggyBac and positive selectable marker genes are removed. Further, in cells selected in this manner, piggyBac is re-inserted in a different genome region from a target DNA at a frequency as high as 68 to 79%. Moreover, since the piggyBac is an insect-derived transposon, whether the transposition is possible in plant cells as in the cases of mammalian cells has not been revealed.

Accordingly, in order to verify whether unnecessary sequences can be removed by utilizing the piggyBac transposition in plant cells also, the present inventors have constructed a system in which a vector having a reporter gene incorporated in piggyBac is randomly inserted in the genomic DNAs of plant cells. Then, the result of constitutively expressing the transposase in this system has revealed that the inserted reporter gene can be removed together with the piggyBac without leaving a trace (NPLs 2 to 5).

However, in this system, although the efficiency of removing piggyBac randomly inserted in the genomic DNAs of the plant cells is approximately 72%, the percentage of the piggyBac removed but inserted again into the genomic DNAs is as high as 41%. Thus, when this system is utilized to introduce only a required mutation into a target DNA of plant cells, further operations are required to remove cells in which piggyBac is re-inserted in regions other than the target DNA.

CITATION LIST

Non Patent Literature

[NPL 1] Yusa Kosuke, et al., "Targeted gene correction of α1-antitrypsin deficiency in induced pluripotent stem cells," Nature, 2012 Apr. 20, Vol. 478, Iss. 7369, pp. 391 to 394

[NPL 2] Nishizawa-YokoiAyako and Toki Seiichi, "Development of marker gene removal system using transposon without leaving footprint in plants," proceedings of the 54th Annual Meeting of The Japanese Society of Plant Physiologists, 2013 Mar. 14

[NPL 3] Nishizawa-YokoiAyako, Toki Seiichi, "Precision genome engineering in rice," proceedings of Keystone Symposia, 2013 Mar. 17

[NPL 4] Nishizawa-YokoiAyako, Toki Seiichi, "Development of marker gene removal system using transposon without leaving footprint in plants," Breeding Research, 2013 Mar. 27, Vol. 15, p. 172

[NPL 5] Saika Hiroaki, Toki Seiichi, "Development and application of new genome modification technique in plants," Bioscience & industry, 2013 May, Vol. 71, No. 3, pp. 275 to 278

SUMMARY OF INVENTION

Technical Problem

The present invention has been made in view of the problems of the above-described conventional techniques. An object of the present invention is to provide a method and so forth enabling an introduction of only a required mutation into a target DNA in a plant cell without leaving any unnecessary sequence such as a marker gene not only in the target DNA but also in regions other than the DNA.

Solution to Problem

The present inventors have earnestly studied in order to achieve the above object. As a result, the inventors have come up with an idea of a system shown in FIG. 1 for enabling an introduction of only a required mutation into a target DNA in a plant cell without leaving any unnecessary sequence such as a marker gene.

To be more specific, first, as shown in a first step in FIG. 1, homologous recombination is allowed to occur by introducing into plant cells a DNA construct comprising a DNA homologous to a target DNA, wherein a desired mutation is introduced and a piggyBac containing a marker gene is inserted in the DNA.

Then, a plant cell, in which the mutation and the piggyBac are introduced in the target DNA via homologous recombination, is selected by screening based on an expression of the marker gene.

Further, as shown in a second step in FIG. 1, a transposase is constitutively expressed in the cell selected as described above. Thereby, the marker gene inserted via the homologous recombination is removed together with the piggyBac from the target DNA. According to this idea, it is possible to prepare a mutant plant having only a desired mutation in a target DNA.

Hence, the system shown in FIG. 1 was actually constructed to verify the effectiveness. The result has revealed for the first time that an unnecessary sequence (marker gene) inserted in the genomic DNA via homologous recombination can be removed from the plant cell without leaving any trace by utilizing piggyBac. In addition, the efficiency was 90% or more and significantly high in comparison with those from mammals and the efficiency of removing piggyBac randomly inserted in the genomic DNAs of plant cells (see NPLs 1 to 5). Furthermore, in the conventional systems disclosed in these literatures, the percentages of the piggyBac excised by the piggyBac transposase but re-inserted into the genomic DNAs have been as high as approximately 70% in the mammalian systems and approximately 40% in the conventional plant systems. In contrast, the percentage in the system shown in FIG. 1 is surprisingly 1% and quite low. These findings have led to the completion of the present invention.

Thus, the present invention relates to: a method for producing a plant cell comprising only a required mutation introduced in a target DNA without leaving any unnecessary sequence such as a marker gene not only in the target DNA but also in regions other than the DNA; a plant cell produced by the method; and a kit and so forth for use in the production method. More specifically, the present invention provides the following inventions.

(1) A method for producing a plant cell comprising a mutation introduced in a target DNA, the method comprising the following steps (i) to (iii):
  (i) a step of introducing into plant cells a DNA construct comprising a DNA homologous to a target DNA, wherein a desired mutation is introduced and a piggyBac transposon containing a marker gene is inserted in the homologous DNA;
  (ii) a step of selecting a plant cell, in which the mutation and the piggyBac transposon are introduced in the target DNA via homologous recombination, based on an expression of the marker gene; and
  (iii) a step of removing the piggyBac transposon from the target DNA by constitutively expressing a piggyBac transposase in the cell selected in the step (ii).

(2) A plant cell comprising a desired mutation and a piggyBac transposon containing a marker gene introduced in a target DNA via homologous recombination by introducing a DNA construct comprising a DNA homologous to the target DNA, wherein the mutation is introduced and the piggyBac transposon is inserted in the homologous DNA.

(3) A plant cell comprising a mutation introduced in a target DNA, and produced by the method according to (1).

(4) A plant comprising the cell according to (2) or (3).

(5) A plant which is any one of a progeny and a clone of the plant according to (4).

(6) A propagation material of the plant according to (4) or (5).

(7) A DNA construct comprising a DNA homologous to a target DNA, wherein a desired mutation is introduced and a piggyBac transposon containing a marker gene is inserted in the homologous DNA.

(8) A kit for use in the method according to (1), the kit comprising the following (a) and (b):
  (a) the DNA construct according to (7); and
  (b) a DNA construct for constitutively expressing a piggyBac transposase in a plant cell.

Advantageous Effects of Invention

The present invention makes it possible to remove an unnecessary sequence together with the piggyBac transposon inserted into the genomic DNA in a plant cell via homologous recombination without leaving any trace. Moreover, the efficiency is significantly as high as 90% or more. Further, the percentage of the piggyBac transposon excised by the piggyBac transposase but re-inserted into the genomic DNA is 1% and quite low. Thus, the present invention makes it possible to introduce only a required mutation into a target DNA in a plant cell without leaving any unnecessary sequence such as a marker gene not only in the target DNA but also in regions other than the DNA.

DESCRIPTION OF EMBODIMENTS

<Method for Producing Plant Cell>

Figure 1:
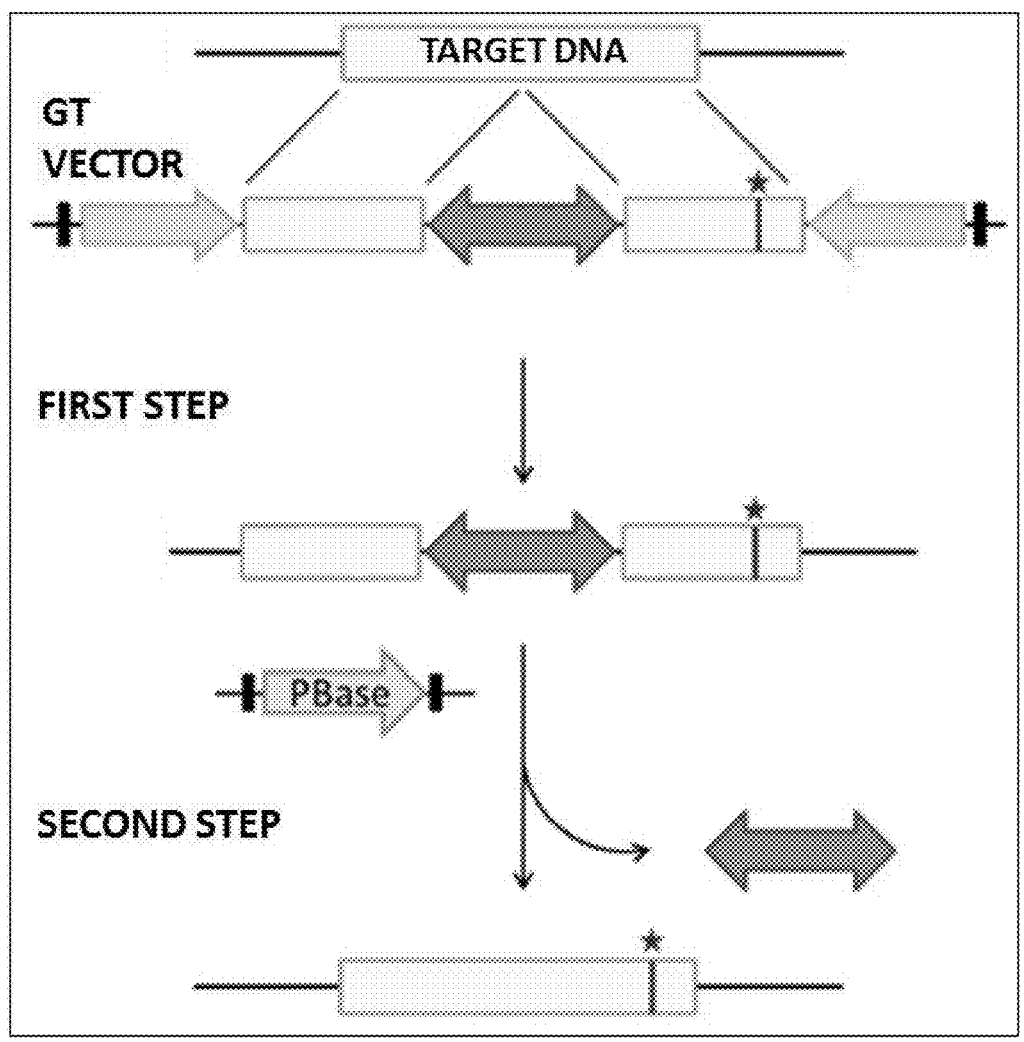
FIG. 1 is a schematic diagram for illustrating a method for producing a plant cell comprising a mutation introduced in a target DNA of the present invention. In the figure, a two-way arrow on a GT vector represents a marker gene (positive selectable marker gene), and a pair of arrows on the GT vector represent negative selectable marker genes. A star indicates a desired mutation site to be introduced into the target DNA. An arrow with PBase represents a DNA encoding a piggyBac transposase. Moreover, black bars provided on both sides of the arrow with PBase and on both sides of the pair of arrows on the GT vector represent right boundary sequences (RB) and left boundary sequences (LB) utilized when DNAs encoding the GT vector and the piggyBac transposase are introduced into a plant cell using *Agrobacterium*.

A method for producing a plant cell of the present invention is a method for producing a plant cell comprising a mutation introduced in a target DNA, the method comprising the following steps (i) to (iii):

(i) a step of introducing into plant cells a DNA construct comprising a DNA homologous to a target DNA, wherein a desired mutation is introduced and a piggyBac transposon containing a marker gene is inserted in the homologous DNA;

(ii) a step of selecting a plant cell, in which the mutation and the piggyBac transposon are introduced in the target DNA via homologous recombination, based on an expression of the marker gene; and (iii) a step of removing the piggyBac transposon from the target DNA by constitutively expressing a piggyBac transposase in the cell selected in the step (ii).

Moreover, the method makes it possible to introduce only a required mutation into a target DNA in a plant cell without leaving any unnecessary sequence such as a marker gene, as described later in Examples.

The "DNA construct" to be introduced into plant cells in order to introduce a mutation to a target DNA in the step (i) is a DNA construct comprising a DNA homologous to a target DNA, wherein a desired mutation is introduced and a piggyBac transposon containing a marker gene is inserted in the homologous DNA.

In the present invention, the term "target DNA" means a DNA on a genome to which a mutation is to be introduced. Any target DNA can be selected from the genomic DNA of a plant cell, and may be a DNA encoding a protein, or may be a DNA encoding a non-coding RNA such as a functional RNA. Further, the target DNA includes not only regions (such as UTR) encoding no protein or non-coding RNA, but also regions regulating expressions of non-coding RNAs and transcription products encoding proteins. Additionally, the target DNA is normally an endogenous DNA, but may be a DNA exogenously inserted into the genomic DNA of a plant cell.

The "mutation" to be introduced into the target DNA is not particularly limited, and may be a silent mutation or may be a null mutation such as a nonsense mutation, a frameshift mutation, an insertion mutation, or a splice site mutation. Moreover, examples of the mutation in the target DNA include deletion, substitution, addition, and/or insertion of one or more nucleotides in the DNA. Further, the number of mutations in the target DNA is not particularly limited, and may be one or more than one.

The term "DNA homologous to a target DNA" means a DNA having a homology with the above-described target DNA on the genome. In the DNA construct of the present invention, the "DNA homologous to a target DNA" is added to each end of a piggyBac transposon to be described later.

Moreover, the number of nucleotides in the DNA homologous to a target DNA should be such a number that homologous recombination can occur between the homologous DNA and the target DNA. Normally, the DNAs homologous to a target DNA and each having 500 to 7000 nucleotides (preferably 1000 to 5000 nucleotides, more preferably 2000 to 4000 nucleotides, and furthermore preferably approximately 3000 nucleotides (for example, 2500 to 3500 nucleotides)) are added respectively to both sides of the piggyBac transposon.

In the present invention, the term "piggyBac transposon" refers to a DNA derived from a moth called *Trichopulsia ni* in Lepidopteran, and excised from the genomic DNA by a piggyBac transposase to be described later. To be more specific, the "piggyBac transposon" refers to a DNA at both ends of which piggyBac inverted-repeat transposable elements (IVRs) recognized specifically by the transposase are disposed. Examples of one or the other of the IVRs include DNAs having a nucleotide sequence of SEQ ID NO: 1 (ccctagaaagata), SEQ ID NO: 2 (ccctagaaagatagtctgcgtaaaattgacgcatg), SEQ ID NO: 3 (ccctagaaagataatcatattgtgacgtacgttaaagataatcatgcgtaaaattgacgcatg), SEQ ID NO: 4 (catgcgtcaattttacgcatgattatctttaacgtacgtcacaatatgattatctttctaggg), or SEQ ID NO: 5 (catgcgtcaattttacgcagactatctttctaggg). Moreover, DNAs having sequences having a high homology with these nucleotide sequences are also utilizable as the IVRs in the present invention, as long as the transposase can specifically recognize the DNAs.

Further, the distance between the IVRs should be equivalent to the number of nucleotides which allow homologous recombination to occur, and also which can be excised by the piggyBac transposase. Although the distance depends also on the number of nucleotides of a marker gene to be inserted as described later or the like, the distance is normally within 1 to 10000 nucleotides.

Furthermore, the "piggyBac transposon" of the present invention contains a marker gene for selecting a plant cell comprising the target DNA via homologous recombination, based on an expression of the marker gene. To put it differently, the IVRs are added to both ends of the marker gene.

The expression of the "marker gene" contained in the piggyBac transposon should serve as an indicator for efficiently selecting a small number of transformed cells comprising the target DNA out of a large number of non-transformed cells. Examples thereof include genes encoding proteins essential for the growth of the modified cells or proteins for promoting the growth (in other words, positive selectable marker genes such as chemical resistance genes), and reporter genes such as a luciferase gene, a GFP gene, a CFP gene, a YFP gene, and a DsRed gene. From the viewpoint of requiring no complicated operation (for example, FACS screening) for detecting the marker gene expression, chemical resistance genes are preferable. Examples of the chemical resistance genes include chemical resistance genes such as a hygromycin resistance gene (hygromycin phosphotransferase gene, hpt), a kanamycin resistance gene, and a neomycin resistance gene; and herbicide resistance genes such as an ALS (AHAS) gene and a PPO gene. Among these, a hygromycin resistance gene is preferable from the viewpoint that the selection efficiency is high in the transformation using rice calli.

Moreover, in the DNA construct of the present invention, a regulatory region for expressing a protein encoded by the marker gene introduced in the plant cell is operably linked to the gene.

For constitutive expression of the protein, examples of the regulatory region include promoters such as a cauliflower mosaic virus (CaMV) 35S promoter, a nopaline synthase gene promoter, a corn-derived polyubiquitin-1 promoter, a rice-derived actin promoter, and a rice-derived elongation factor 1α promoter; and terminator sequences for terminating the transcription of genes induced by the promoters or the like (such as a rice-derived heat shock protein 17.3 terminator, a rice-derived heat shock protein 16.9a terminator, a rice-derived actin terminator, a nopaline synthase gene terminator, an octopine synthase (OCS) gene terminator, andaCaMV35S terminator). Further, the regulatory region may contain an enhancer to increase the gene expression efficiency, such as a CaMV35S enhancer, a transcription enhancer E12, or enhancers of an omega sequence or the like.

Moreover, for inducible expression of the protein, it is suitable to use a promoter which induces the expression in response to a stimulus, for example, a rice chitinase gene promoter, a tobacco PR protein gene promoter, a rice lip19 gene promoter, rice hsp80 gene and hsp72 gene promoters, an *Arabidopsis thaliana* rab16 gene promoter, a parsley chalcone synthase gene promoter, a corn alcohol dehydrogenase gene promoter, a promoter which induces the expression in response to a chemical such as tetracycline, estradiol, or dexamethasone, or other similar promoters.

Meanwhile, in addition to the marker gene, another DNA(s) may be inserted in the piggyBac transposon of the present invention, as long as the other DNAs are disposed between the IVRs. The other DNAs are not particularly limited. Nevertheless, an example thereof includes a terminator for inactivating a protein or the like encoded by the target DNA in which the piggyBac transposon is inserted. Moreover, in order to omitting a step of introducing a vector again which expresses the piggyBac transposase to remove the piggyBac from the target DNA after the DNA construct is introduced, the example includes a DNA construct (expression cassette) capable of inducibly expressing the piggyBac transposase.

In the "DNA construct" of the present invention, a gene encoding a protein for inhibiting the growth of the modified cells or a protein for suppressing the growth (in other words, negative selectable marker gene) may be added to both ends of the DNA homologous to the target DNA (see the "GT vector" in FIG. 1).

Examples of the "negative selectable marker gene" include a diphtheria toxin (DT-A) gene, a codA gene, an exotoxin A gene, a ricin toxin A gene, a cytochrome P-450 gene, an RNase T1 gene, and a barnase gene. Among these, a DT-A gene is preferable for rice calli and the like from the viewpoints of the high negative selection efficiency and not affecting the surrounding cells because of the lack of the intracellular movement ability. Moreover, as in the case of the above-described marker gene, a regulatory region for expressing a protein encoded by the negative selectable marker gene introduced in the plant cell is operably linked to the gene in the DNA construct of the present invention.

Further, when the DNA construct containing such a negative selectable marker gene is introduced into a plant cell, the negative selectable marker gene is never inserted into the genomic DNA of the cell as a result of incorporating a portion (the DNA homologous to the target DNA) of the DNA construct into the target DNA via homologous recombination. This is because the negative selectable marker gene is located outside the homologous DNA. Hence, the plant cell can grow without the influence from the gene. On the other hand, if the DNA construct is randomly inserted into the genomic DNA of a plant cell, the negative selectable marker gene may also be inserted therein, so that the growth of the plant cell having such a random insertion may be suppressed or inhibited. Thus, introducing the DNA construct containing the negative selectable marker gene into a plant cell does not cause a random insertion, making it possible to efficiently select the plant cell comprising the mutation introduced in the target DNA via homologous recombination.

Although the "DNA construct" of the present invention has been described above, the method for introducing such a DNA construct into plant cells in the step (i) of the production method of the present invention is not particularly limited. It is possible to use various methods known to those skilled in the art such as an *Agrobacterium*-mediated method, a polyethylene glycol method, an electroporation method (electroporation), and a particle gun method.

Next, in the step (ii) of the production method of the present invention, a plant cell, in which the mutation and the piggyBac transposon are introduced in the target DNA via homologous recombination, is selected based on an expression of the marker gene.

Those skilled in the art can perform such a "selection" by selecting a known approach as appropriate in accordance with the type of the marker gene to be used. For example, in the case of using a chemical resistance gene, if the plant cell having the DNA construct of the present invention introduced in the step (i) is cultured in the presence of a corresponding chemical, a plant cell, in which the mutation and so forth are introduced in the target DNA, can be selected. In the case of using a reporter gene such as a GFP gene, if the plant cell having the DNA construct of the present invention introduced in the step (i) is subjected to FACS or the like, a plant cell, in which the mutation and so forth are introduced in the target DNA, can be selected.

Additionally, besides the selection based on the expression of the marker gene, the step may comprise confirming the introduction of the mutation and the piggyBac transposon into the target DNA via homologous recombination, as described later in Examples, by a PCR method, a sequencing method, a Southern blotting method, a CAPS (cleaved amplified polymorphic sequence) method, or the like.

Next, in the step (iii) of the production method of the present invention, the piggyBac transposon is removed from the target DNA by constitutively expressing a piggyBac transposase in the cell selected in the step (ii) described above.

In the present invention, the "piggyBac transposase" should have an activity of removing the above-described piggyBac transposon from the genomic DNA in the plant cell. An example thereof includes a wild type piggyBac transposase derived from *Trichopulsia ni* (typically, a protein having an amino acid sequence specified under GenBank ACCESSION No: AAA87375).

Meanwhile, the amino acid sequence of the piggyBac transposase may be mutated in nature (i.e., non-artificially). In addition, a mutation can also be introduced artificially. Thus, the present invention includes such mutants also, as long as the mutants have the removal activity. The piggyBac transposase mutant include proteins having the amino acid sequence specified under GenBank ACCESSION No: AAA87375 in which one or more amino acids are substituted, deleted, added, and/or inserted. Herein, "more than one" generally refers to 120 amino acids or less, 100 amino acids or less, 80 amino acids or less, 60 amino acids or less, 40 amino acids or less, 20 amino acids or less, preferably 10 amino acids or less, and more preferably several amino acids or less (for example, 5 amino acids or less, 3 amino acids or less, 2 amino acids or less, 1 amino acid).

Examples of such mutants include proteins having an amino acid sequence specified under GenBank ACCESSION No: AFN89785, ABS12112, ABC88680, ABC88678, ABC88677, ABC88675, ABC88671, or AAE68098.

Moreover, according to the description of "Yusa K. et al., Proc Natl Acad Sci USA., 2011 January, Vol. 108, No. 4, pp. 1531 to 1536," it has been revealed that proteins having the amino acid sequence specified under GenBank ACCESSION No: AAA87375 in which at least one amino acid substitution selected from G2C, Q40R, I30V, G165S, T43A, S61R, S103P, S103T, M194V, R281G, M282V, G316E, I426V, Q497L, N505D, Q573L, S509G, N571S (or N570S), N538K, Q591P, Q591R, and F594L is introduced have higher activities of removing the piggyBac transposon from the genomic DNA than that of the wild type.

Thus, in the present invention also, these proteins having the amino acid sequence in which at least one amino acid substitution is introduced are suitably used. More suitably used is a protein having the amino acid sequence in which I30V, S103P, G165S, M282V, S509G, N571S (or N570S) and N538K are introduced (hyPBase, a protein having an amino acid sequence of SEQ ID NO: 7, which will be described later in Examples).

Moreover, a functional protein may be added to the "piggyBac transposase" in the present invention. Such a functional protein can be directly or indirectly added to one or both of the N-terminal side and the C-terminal side of the piggyBac transposase. The functional protein is not particularly limited, and is selected as appropriate depending on a function to be provided to the piggyBac transposase. Examples thereof include a green fluorescent protein (GFP), a luciferase protein, a FLAG-tag protein (registered trademark, Sigma-Aldrich Co.), and a glutathione-S-transferase (GST) protein for facilitating the detection or the like of the protein. Meanwhile, a nuclear localization signal may be added from the viewpoint that the piggyBac transposase stably functions in the nucleus.

The method for constitutively expressing the piggyBac transposase in the step (iii) is not particularly limited. An example thereof includes a method in which a DNA construct comprising a gene encoding the transposase and a regulatory region for constitutively expressing the gene is introduced into the cell selected in the step (ii). Further, the DNA construct to be introduced is preferably inserted in the genomic DNA of the plant cell from the viewpoint that the piggyBac transposase is constitutively and stably expressed.

As the "regulatory region for constitutively expressing" the piggyBac transposase, it is possible to use the "regulatory regions for constitutive expression" listed in the above description of "the DNA construct of the present invention." Above all, a corn-derived polyubiquitin-1 promoter is preferable among the promoters from the viewpoints that the expression amount is high in any tissue, and particularly that the expression amount is high in dividing cells such as calli.

Moreover, an example of another mode of constitutively expressing the piggyBac transposase in the step (iii) includes a method in which a DNA construct comprising a gene encoding the transposase and a regulatory region for inducibly expressing the gene is introduced into the plant cell followed by culturing in the presence of a stimulus, that is, a condition for inducing the expression.

The timing of introducing the DNA construct for inducibly expressing the piggyBac transposase into the plant cell may be simultaneous with or before the introduction of the above-described DNA construct comprising the DNA homologous to the target DNA in the step (i). Furthermore, the timing may be before the selection based on the expression of the marker gene in the step (ii) or may be after the selection.

In addition, as the "regulatory region for inducibly expressing" the piggyBac transposase, it is possible to use the "regulatory regions for inducible expression" listed in the above description of "the DNA construct of the present invention."

Further, the DNA construct for constitutively expressing a piggyBac transposase (hereinafter the same shall apply to the DNA construct for inducibly expressing a piggyBac transposase) may comprise the above-described reporter gene, chemical resistance gene, and so forth, because the plant cell, in which the DNA construct is introduced, can be efficiently selected.

Furthermore, the method for introducing the DNA construct for constitutively expressing a piggyBac transposase into plant cells is not particularly limited. It is possible to use various methods known to those skilled in the art such as an *Agrobacterium*-mediated method, a polyethylene glycol method, an electroporation method, and a particle gun method.

The piggyBac transposase is then constitutively expressed in the cell selected in the step (ii) as described above, so that the marker gene is removed together with the piggyBac transposon as described later in Examples. This makes it possible to obtain a plant cell comprising only a desired mutation introduced in a target DNA at quite a high frequency (92 to 99%). Further, the percentage of the piggyBac removed in the above described manner but re-inserted into the genomic DNA is 1% and quite low. Accordingly, the present invention does not need a step for removing cells having the re-insertion (negative selection or the like).

<Plant Cell>

As described above, the production method of the present invention makes it possible to obtain a plant cell comprising only a desired mutation introduced in a target DNA at quite a high frequency (92 to 99%). Thus, the present invention provides a plant cell comprising a mutation introduced in a target DNA, and produced by the production method.

Moreover, as described later in Examples, the plant cell comprising the piggyBac transposon inserted in a target DNA via homologous recombination is one prepared for the first time in the present invention. This is useful in preparing a plant cell comprising only a desired mutation introduced in a target DNA, as described above. Thus, the present invention also provides a plant cell comprising a desired mutation and a piggyBac transposon containing a marker gene introduced in a target DNA via homologous recombination by introducing a DNA construct comprising a DNA homologous to the target DNA, wherein the mutation is introduced and the piggyBac transposon is inserted in the homologous DNA.

In the present invention, the term "plant" is not particularly limited. Examples thereof include monocot plants such as rice (*Oryza sativa*), wheat (*Triticum* spp.), barley (*Hordeum vulgare*), and corn (*Zea mays*); and dicot plants such as tobacco (*Nicotiana tabacum*), potato (*Solanum tuberosum*), eggplant (*Solanum melongena*), and rapeseed (*Brassica napus*). Moreover, the term "plant cell" includes cells in a plant, besides culture cells. Further, examples thereof include plant cells in various forms, for example, suspended culture cells, protoplasts, leaf sections, calli, immature embryos, pollens, and the like.

<Plant etc.>

A plant can be obtained by regenerating the plant cell of the present invention. Particularly, since the plant cell produced by the production method of the present invention has only a desired mutation in a target DNA, a plant regenerated from such a plant cell has a phenotype changed by the mutation. Thus, utilization of the method of the present invention enables efficient plant breeding as well as efficient function analysis of the target DNA.

A plant can be regenerated from the plant cell by methods known to those skilled in the art in accordance with the type of the plant cell. An example for *Arabidopsis* includes the method described in Akama et al. (Plant Cell Reports 12: 7-11, 1992); for rice, examples include the methods described in Datta (In Gene Transfer To Plants (Potrykus I and Spangenberg Eds.) pp 66-74, 1995), Toki et al. (Plant Physiol. 100: 1503-1507, 1992), Christou et al. (Bio/technology, 9: 957-962, 1991), and Hiei et al. (Plant J. 6: 271-282, 1994); for barley, examples include the methods described in Tingay et al. (Plant J. 11: 1369-1376, 1997), Murray et al. (Plant Cell Report 22: 397-402, 2004), and Travalla et al. (Plant Cell Report 23: 780-789, 2005); for corn, examples include the methods described in Shillito et al. (Bio/Technology, 7: 581, 1989) and Gorden-Kamm et al. (Plant Cell 2: 603, 1990); for tomato (*Solanum lycopersicum*), an example includes the method described in Matsukura et al. (J. Exp. Bot., 44: 1837-1845, 1993); for soy bean (*Glycine max*), an example includes the method described in Patent Literature (U.S. Pat. No. 5,416,011); for potato, an example includes the method described in Visser et al. (Theor. Appl. Genet, 78: 594, 1989); and for tobacco, an example includes the method described in Nagata and Takebe (Planta, 99: 12, 1971). For plants other than those listed here, those skilled in the art can regenerate the plants by employing, for example, the methods described in "Protocols for Plant Transformation" edited by Tabei Yutaka (published by Kagaku-Dojin Publishing Company, INC.).

Once a plant comprising the cell comprising a mutation introduced in a target DNA is obtained as described above, a progeny can be obtained from the plant by sexual reproduction or asexual reproduction. Moreover, a propagation material (for example, a seed, a fruit, a spike, a stub, a callus, a protoplast, or the like) is obtained from the plant or a progeny or a clone thereof, from which mass production of the plant is also possible. Thus, the present invention includes: a plant comprising the plant cell of the present invention; a progeny and a clone of the plant; and a propagation material of the plant, the progeny, and the clone.

Meanwhile, although only a desired mutation is introduced in the target DNA of the plant cell produced by the production method of the present invention, the DNA encoding the exogenously-introduced piggyBac transposase remains in the cell. Nevertheless, crossing the plant comprising the plant cell produced by the production method of the present invention with a wild type plant and then backcrossing enable removal of the DNA encoding the piggyBac transposase, too.

Additionally, the present invention also provides a processed product produced from any of the plant cell, the plant, and the propagation material of the present invention. In the present invention, the processed product is not particularly limited, and refers to processed products in general, which have been conventionally produced from plants. Examples thereof include liquid extracts from plants, and plant dried powders and processed foods. More concretely, the examples include, in a case of rice, cooked rice, rice crackers, and the like; in a case of wheat, breads, noodles, and the like; in a case of corn, corn oil, corn starch, corn chips, and the like; in a case of soybean, soybean oil, tofu, natto, and the like; in a case of potato, potato chips, starches, and the like; in a case of tomato, ketchup and the like; and in a case of canola, canola oil and the like.

<Kit etc.>

As described above, the DNA construct of the present invention is useful in the production method of the present invention, and the effectiveness is also demonstrated for the first time in the present invention. Thus, the present invention also provides a DNA construct comprising a DNA homologous to a target DNA, wherein a desired mutation is introduced and a piggyBac transposon containing a marker gene is inserted in the homologous DNA.

In addition, as described above, a DNA construct for constitutively expressing a piggyBac transposase in a plant cell is also useful in the production method of the present invention. Thus, the present invention also provides a kit for use in the production method of the present invention, the kit comprising the following (a) and (b):

(a) a DNA construct comprising a DNA homologous to a target DNA, wherein a desired mutation is introduced and a piggyBac transposon containing a marker gene is inserted in the homologous DNA; and (b) a DNA construct for constitutively expressing a piggyBac transposase in a plant cell.

Although each of these DNA constructs is as described above in the steps (i) and (iii) of the production method of the present invention, the form thereof may be a single-stranded DNA or a double-stranded DNA. Alternatively, the form may be a linear DNA or a circular DNA, and the DNA construct scan be prepared in a form suitable for the above-described introduction method into a plant cell.

For example, when *Agrobacterium* is used for the introduction into a plant cell, examples of the form of the DNA constructs include pBI-based, pPZP-based, or pSMA-based vectors, and other similar vectors. Moreover, examples of a more preferable form include vectors of binary vector systems (such as pZHG, pKOD4, pBI121, pBI101, pBI101.2, pBI101.3, pBIG2113).

Meanwhile, for the introduction into a plant cell by other methods such as an electroporation method, examples of the form of the DNA construct include pUC-based vectors such as pUC18, pUC19, and pUC9. Further, the DNA constructs may take a form of a plant virus vector such as CaMV, bean golden mosaic virus (BGMV), or tobacco mosaic virus (TMV).

Moreover, those skilled in the art can prepare such DNA constructs as appropriate by utilizing known genetic recombination techniques such as a PCR method, a restriction enzyme treatment, and a cloning method as described later in Examples. Additionally, the DNA constructs can also be chemically synthesized by using a commercially-available automated DNA sequence synthesizer or the like.

Further, in preparing the DNA construct according to (a), those skilled in the art can introduce a desired mutation into the DNA homologous to a target DNA by site-directed mutagenesis (for example, the method described in Kunkel, TA (1985) Proc Natl Acad Sci USA. 82, 488-492) or the like.

In addition, as described above, the piggyBac transposase is a protein derived from a moth. Hence, from the viewpoint of expressing the piggyBac transposase in a plant cell at a high level, a DNA encoding the piggyBac transposase optimized for a codon usage frequency of a plant, into which the DNA construct is introduced, may be inserted in the DNA construct according to (b).

EXAMPLES

Hereinafter, the present invention will be more specifically described on the basis of Examples. However, the present invention is not limited to the following Examples.

The present inventors have previously created herbicide bispyribac sodium (BS)-tolerant rice plants successfully by introducing two point mutations, which cause two amino acid changes, into the acetolactate synthase (ALS) locus via gene targeting (GT) (see Endo M. et al., The Plant Journal, 2007, Vol. 52, pp. 157 to 166).

Note that the two point mutations in the ALS gene are: a mutation (W548L) in which TGG encoding tryptophan at position 548 is changed to TTG encoding leucine; and a mutation (S627I) in which AGT encoding serine at position 627 is changed to ATT encoding isoleucine. In addition, although it is rare that GT occurs to introduce these point mutations, GT-occurring cells were easily selected by culturing in a medium containing BS.

However, such a selection cannot be performed in introducing mutations into many target DNAs. Against this background, the inventors have come up with the idea of the system as shown in FIG. 1 to establish a universal strategy for preparing a mutant plant having only a desired mutation in a target DNA.

To be more specific, first, as shown in the first step in FIG. 1, homologous recombination is allowed to occur by introducing into plant cells a DNA construct comprising a DNA homologous to a target DNA, wherein a desired mutation is introduced and a piggyBac containing a marker gene (positive selectable marker gene) is inserted in the homologous DNA.

Note that, in this event, disposing a negative selectable marker gene outside the homologous DNA eliminates cells in which the DNA construct is randomly inserted in regions other than the target DNA.

In addition, a plant cell, in which the mutation and the piggyBac are introduced in the target DNA via homologous recombination, is selected by screening based on an expression of the positive selectable marker gene.

Then, as shown in the second step in FIG. 1, if the positive selectable marker gene inserted via the homologous recombination can be removed together with the piggyBac from the target DNA by constitutively expressing a piggyBac transposase in the cell selected as described above, this makes it possible to prepare a mutant plant having only a desired mutation in a target DNA.

Hence, the system shown in FIG. 1 was constructed to verify the effectiveness by the method described below. Note that, as the target DNA and the mutation introduced into the DNA in the present Examples, the above-described rice ALS gene and two point mutations (W548L and S627I) were selected. In addition, as the positive selectable marker gene and the negative selectable marker gene, a hygromycin phosphotransferase gene (hpt) and a diphtheria toxin gene (DT-A) were used, respectively.

Example 1

<Construction of GT Vector>

To prepare a mutant plant having only a desired mutation in a target DNA, a DNA construct (GT vector) was constructed as follows, the DNA construct comprising a DNA homologous to the target DNA, wherein the desired mutation was introduced and a piggyBac transposon containing a marker gene was inserted in the homologous DNA.

First, the T-DNA described in "Endo M. et al., 2007" was treated with HpaI and EcoRI. Thereby, 9.4-kb long fragments containing the ALS gene harboring the two point mutations were excised and incorporated into a SnaBI recognition site and an EcoRI recognition site of pENTR L1/L2 (manufactured by Life Technologies Corporation).

Next, a piggyBac inverted-repeat transposable element (IVR) containing the recognition site of a meganuclease I-SecI was introduced to a HpaI recognition site in the ALS gene and cloned to prepare pE(L1-L2)mALSpb. Regarding the IVR containing the I-SecI recognition site, see Nishizawa-Yokoi A. et al., The Plant Journal, 2014 February, Vol. 77, Iss. 3, pp. 454 to 463 (published online on 2013 Dec. 9). Moreover, the introduction of the HpaI recognition site into the ALS gene was performed using the following primer set by expression-PCR (E-PCR) (see Lanar D E. and Kain K C., PCR Methods Appl., 1994 October, Vo. 4, No. 2, S92-96).

(SEQ ID NO: 8)
5'-tgctggatgagttaacgaaaggtgagg-3'
and (SEQ ID NO: 9)
5'-cctcacctttcgttaactcatccagca-3'.

Next, a 4.3-kb long fragment containing a rice-derived actin terminator, a cauliflower mosaic virus 35S promoter, the hygromycin phosphotransferase gene (hpt), and a rice-derived heat shock protein 17.3 terminator was digested with I-SceI and inserted into pE(L1-L2)mALS. Thus, pE(L1-L2)mALSpHPTb was prepared.

Next, an 11.3-kb long fragment contained in the mALSpHPTb was introduced into a gene targeting binary vector pKOD4 containing two diphtheria toxin (DT-A) expression cassettes and re-cloned by a Gateway LR Clonase II reaction (registered trademark, manufactured by Life Technologies Corporation). Thus, pKOD4/mALS was prepared. The pKOD4 is a vector derived from pZHG. Regarding pZHG, see Osakabe K. et al., "A Mutated Cytosine Deaminase Gene, codA (D314A), as an Efficient Negative Selection Marker for Gene Targeting in Rice", Plant & Cell Physiology, published on line on 2014 Jan. 22. As the DT-A expression cassettes, "corn-derived polyubiquitin-1 promoter+DT-A+rice-derived heat shock protein (hsp) 16.9a terminator" and "rice-derived elongation factor 1α promoter+DT-A+rice-derived hsp 16.9a terminator" were used (see Terada R. et al., Nat Biotechnol., 2002, Vol. 20, pp. 1030 to 1034).

The GT vector pKOD4/mALS constructed as described above harbored a 6.4-kb long fragment containing an ALS coding region and the cassettes for expressing the DT-A gene as the negative selectable marker gene. In addition, as described above, in the ALS coding region, besides the mutations specified as W548L and S627I, a silent mutation (change from GCTGAC to GAATTC) for introducing the HpaI recognition site was also introduced at 301 bp upstream of W548L. Note that the silent mutation was introduced so as to insert the rice-derived actin terminator, and the piggyBac transposon harboring a cassette for expressing the hpt gene as the positive selectable marker gene. In addition, after the homologous recombination with this GT vector, the ALS gene was split by the insertion of the hpt gene expression cassette, and inactivated.

Example 2

Next, the GT vector was used to prepare a plant having only a desired mutation in a target DNA by the method described below.

To be more specific, first, the GT vector (pKOD4/mALS vector) was introduced into an *Agrobacterium tumefaciens* strain EHA105 (see Hood E. et al., Transgenic Research, 1993, Vol. 2, Iss. 4, pp. 208 to 218) by an electroporation method.

Next, using the obtained *Agrobacterium*, rice calli (4-week-old calli derived from Nipponbare) were transformed according to the method described in "Toki S. et al., The Plant Journal, 2006, Vol. 47, pp. 969 to 976."

Then, according to the method described in "Saika H. et al., Plant Physiology, 2011, Vol. 156, pp. 1269 to 1277," the GT transformation was performed on the rice. To be more specific, the rice calli transformed with the *Agrobacterium* harboring the above-described pKOD4/mALS were cultured for 4 weeks on a callus induction medium for the selection. Note that the medium used was an N6D medium supplemented with 50 mg/L of hygromycin and 25 mg/L of meropenem (both manufactured by Wako Pure Chemical Industries, Ltd.) and solidified with 0.4% Gelrite (registered trademark, manufactured by Wako Pure Chemical Industries, Ltd.). In addition, as a result, 100 independent hygromycin-tolerant calli were successfully selected from 3259 calli as shown in Table 1.

TABLE 1

| Experiment | The number of calli infected with Agrobacterium | The number of hygromycin-tolerant calli | The number of calli having undergone homologous recombination | The number of calli in which W548L/S627I mutations were introduced |
|---|---|---|---|---|
| A | 1,463 (7.53 g) | 25 | 1 | 1 |
| B | 1,796 (11.85 g) | 75 | 5 | 3 |
| Total | 3,259 (19.38 g) | 100 | 6 | 4 |

Further, to identify transgenic calli having the GT events at the ALS locus, the obtained hygromycin-tolerant calli were subjected to the following screening by PCR and sequencing analysis.

<PCR>

Figure 2:
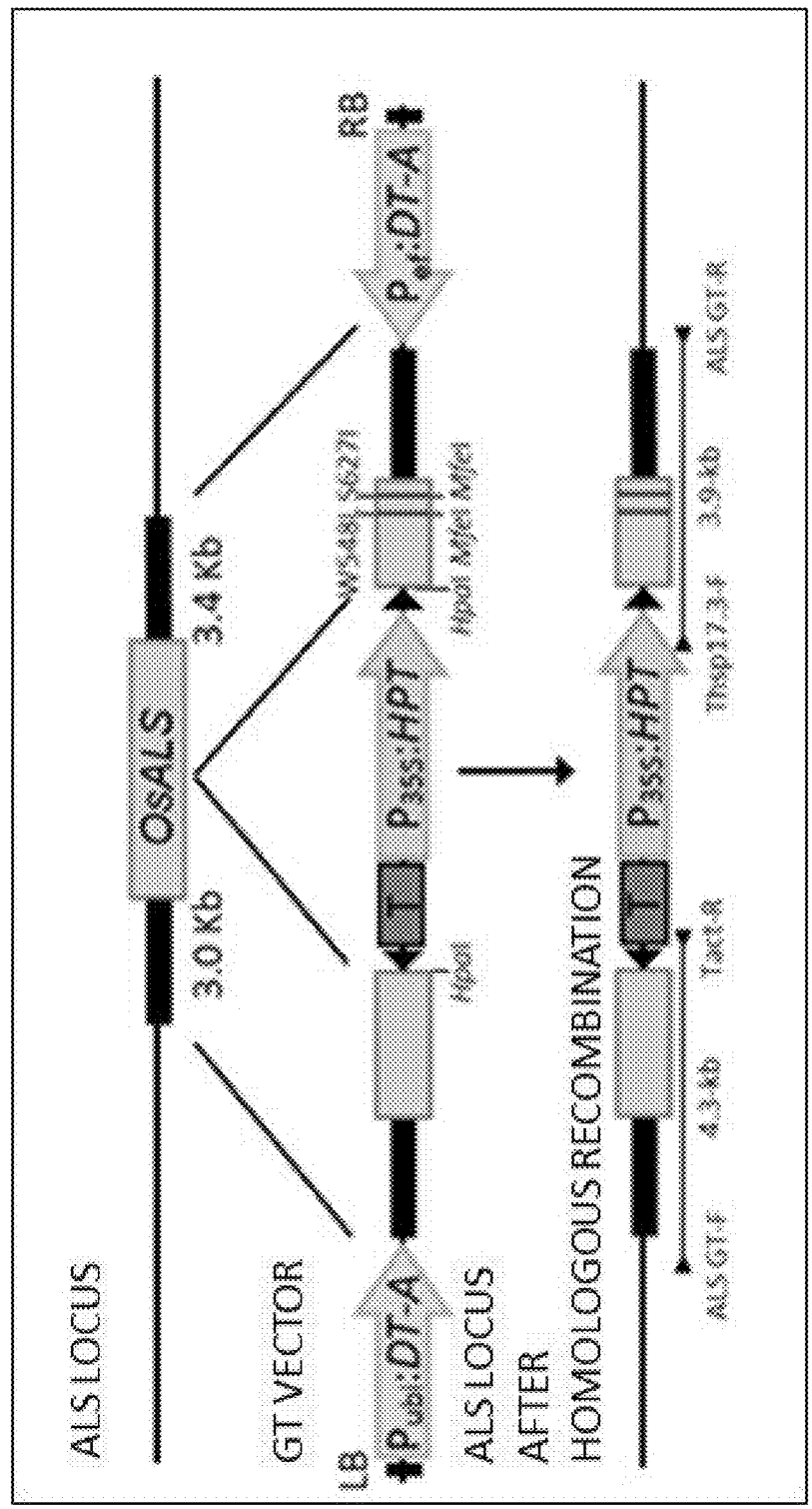
FIG. 2 is a schematic diagram showing a scheme for verifying the effectiveness of targeting a rice-derived ALS gene (OsALS) by the method for producing a plant cell comprising a mutation introduced in a target DNA of the present invention.

From a small mass of each rice callus, the genomic DNA was extracted using Agencourt Chloropure (manufactured by BECKMAN COULTER Inc.) according to the attached maker protocol. Then, using the extracted genomic DNA as a template, the PCR amplification was carried out with KOD FX or KOD FX Neo (manufactured by TOYOBO CO., LTD.) and primer sets shown below (regarding the annealing positions of the ALS locus and the primers, see FIG. 2).

```
ALS gene 5'amplification primer set:
ALS GT-F
                                        (SEQ ID NO: 10)
(5'-gacatgacaaccagtcatccgattaggttt-3')
and Tact-R
                                        (SEQ ID NO: 11)
(5'-ctgacgatgagaatatatctgatgctgtga-3')

ALS gene 3'amplification primer set:
Thsp17.3-F
                                        (SEQ ID NO: 12)
(5'-acatacccatccaacaatgttcaatccctt-3')
and ALS GT-R
                                        (SEQ ID NO: 13)
(5'-tctggagatagcatacttgctttgcttggt-3').
```

Subsequently, as a result of this PCR, upstream and downstream junction fragments were detected in six independent calli as shown in Table 1. It was confirmed that, in these calli, the positive selectable marker gene was introduced in the ALS locus by the homologous recombination between the GT vector and the target DNA.

<Sequencing Analysis>

Next, a 4,302-bp long fragment obtained by amplifying a 5' side of the ALS gene and a 3,943-bp long fragment obtained by amplifying a 3' side of the gene were introduced to a pCR-Blunt II-TOPO vector (manufactured by Life Technologies Corporation) by a TOPO cloning method and cloned for the sequencing analysis.

Concretely, universal primers M13-R (5'-caggaaacagctatgac-3' (SEQ ID NO: 14)) and M13-F (5'-gtaaaacgacggccagt-3' (SEQ ID NO: 15)) were used to confirm whether the junction sequences were as expected or not.

In addition, whether or not the W548L and S627I mutations were present in the 3,943-bp long fragment was checked using primers ALS-R1 (5'-acttgggatcataggcagca-3' (SEQ ID NO: 16)) and ALS-R2 (5'-ccttagcagtcaggaatagcttg-3' (SEQ ID NO: 17)), respectively.

Then, as a result of this sequencing analysis, a lack of the W548L mutation and a lack of the W548L/S627I mutations were detected respectively in two callus lines as shown in Table 1.

Thus, finally, four callus lines (A, B1, B2, B3, and B4), in which the introduction of the W548L and S627I mutations was confirmed, were identified as GT candidate calli. Among these, two lines (A and B1) were subjected to a piggyBac removal treatment described below.

<piggyBac Removal Treatment>

The calli (GT candidate callus lines A and B1), in which the introduction of the W548L and S627I mutations was confirmed, were transferred to an N6D medium not supplemented with hygromycin and meropenem, and cultured for 4 weeks.

Next, in order to remove the piggyBac containing the positive selectable marker gene (hpt) from the target DNA, the GT candidate calli were infected with *Agrobacterium* harboring a pPN/hyPBase expression vector. Note that the expression vector encodes a hyperactive piggyBac transposase (hyPBase, see NPL 1) whose expression is induced by the corn-derived polyubiquitin-1 promoter (see supra "Nishizawa-Yokoi A. et al, 2014 February).

Then, after the transformation, the calli were cultured on an N6D medium supplemented with 35 mg/L of geneticin (manufactured by Nacalai Tesque, Inc.) and 25 mg/L of meropenem. Thus, five or six lines of calli constitutively expressing the hyPBase (GT_hy calli) were selected from the GT candidate callus lines (GT lines A_hy: 5, 6, 10, 13, and 24; GT lines B1_hy: 5, 9, 11, 12, 19, and 20).

Next, the GT_hy calli obtained as described above were transferred to a re-differentiation medium supplemented with 25 mg/L of meropenem. Then, shoots arising from the calli were transferred to a Murashige & Skoog medium (see Murashige T. and Skoog F., Physiologia Plantarum, 1962, Vol. 15, Iss. 3, pp. 473 to 497) not supplemented with plant hormones, and cultured. Thus, T0 re-differentiated plants were obtained from the calli of the 11 lines. From each line, 20 individuals were prepared.

Test Example 1

<Verification 1 of Marker Removal from Target DNA with piggyBac>

In order to evaluate the efficiency of removing the positive selectable marker gene via the piggyBac transposition in the T0 re-differentiated plants prepared in Example 2, the marker removal analysis was performed based on cleaved amplified polymorphic sequence (CAPS) (see supra "Endo M. et al, 2007").

To be more specific, first, the genomic DNA was extracted from leaves of each GT line A_hy and GT line B1_hy. Using the genomic DNA as a template, a 3,833-bp long piggyBac-removed fragment was amplified by PCR with PrimeSTAR GXL DNA Polymerase (manufactured by TAKARA) and a primer set (ALS-F1 and ALS GT-R). Then, the PCR products were treated with MfeI and gel electrophoresed to detect the patterns of the resulting cleaved fragments. Moreover, in order to analyze the frequency of the piggyBac re-inserted, the PCR analysis was carried out using the genomic DNA as a template and using PrimeSTAR GXL DNA Polymerase (manufactured by TAKARA) and a primer set for specifically detecting the marker gene: HPT-F (5'-caaagatcgttatgtttatcggcactttg-3' (SEQ ID NO: 18)) and HPT-R (5'-ctcgagctatttctttgccctc-3' (SEQ ID NO: 19)). Table 2 shows the obtained result of the GT lines A_hy, and Table 3 shows that of the GT lines B1_hy.

Note that the ALS-F1 (5'-gtacgcaaattatgccgtgga-3' (SEQ ID NO: 20)) is a primer which anneals to 359 bp upstream of the piggyBac insertion site. The ALS GT-R is a primer which is specific to the endogenous ALS locus (3,478 bp downstream of the piggyBac insertion site) (regarding the annealing positions of the ALS locus and the primers, see FIG. 3). Additionally, an 8,726-bp long fragment containing the marker gene cannot be amplified with these primers (see FIG. 3).

Moreover, since the two point mutations of W548L and S627I in the ALS locus generate the recognition site (CAATTG) of the restriction enzyme MfeI, the presence or absence of GT can be easily detected based on the presence or absence of the cleavage with the restriction enzyme.

Figure 3:
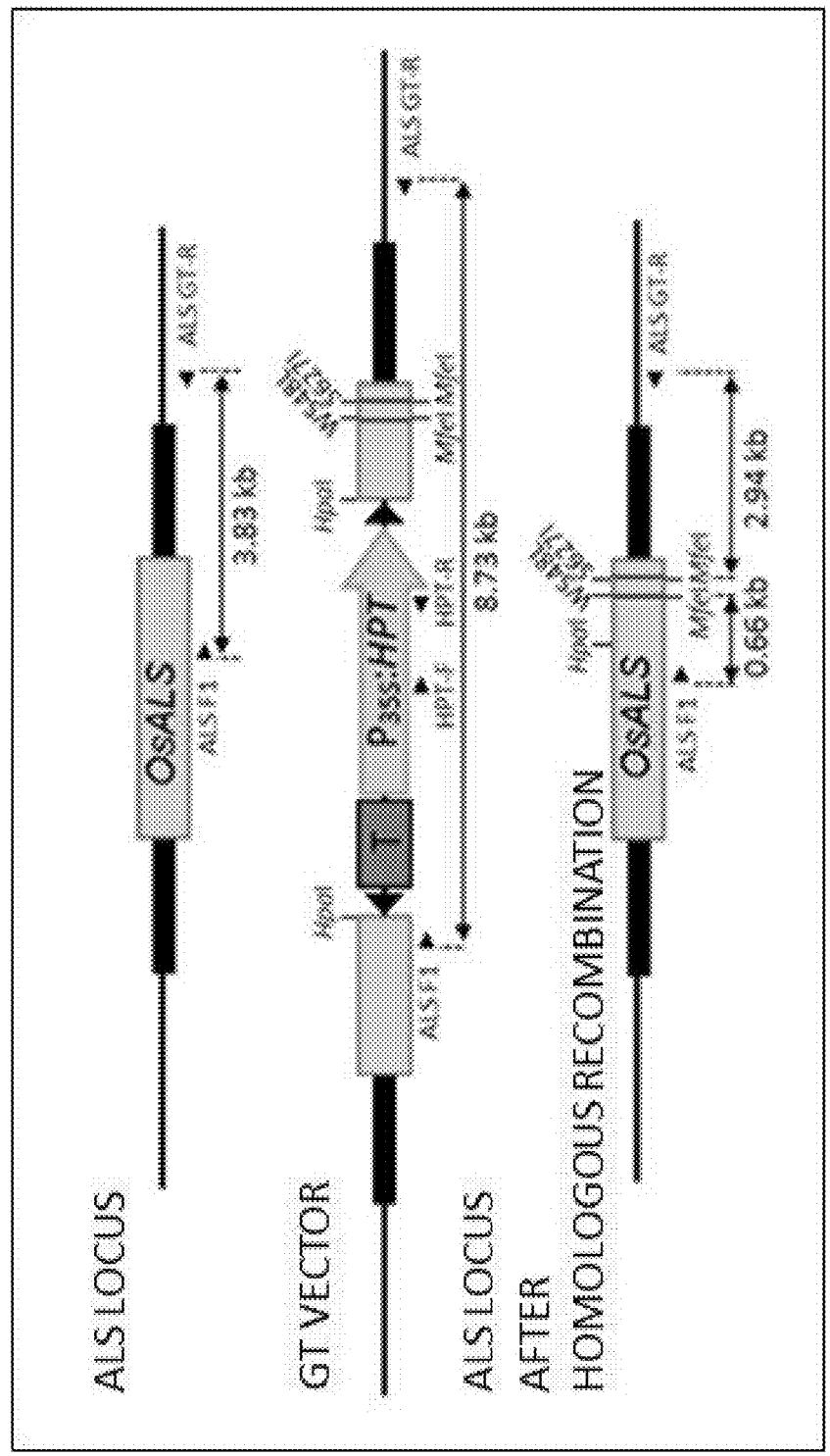
FIG. 3 is a schematic diagram showing fragments and lengths thereof expected to be detected when the rice-derived ALS locus, the GT vector, and the ALS locus containing only desired two point mutations (W548L and S627I) introduced by homologous recombination with the vector followed by piggyBac transposon removal are analyzed by a CAPS (cleaved amplified polymorphic sequence) method using a restriction enzyme MfeI.

Further, if the piggyBac is removed from the target ALS locus by the expression of the hyPBase, 2938-bp, 657-bp and 238-bp long fragments are to be detected as a result of the PCR amplification using the primer set of ALS F1 and ALS GT-R and the subsequent MfeI treatment (see FIG. 3).

Furthermore, in T0 re-differentiated plants heterozygous for the ALS locus, in addition to the three fragments, a 3833-bp long fragment is also detected which will not be cleaved by the MfeI (see FIG. 3). On the other hand, in plant individuals expressing the hyPBase, if the piggyBac remains in the target ALS locus, an 8,726-bp fragment, which contains the marker gene sequence but cannot be amplified under the above-described PCR conditions, is expected to be detected (see FIG. 3).

TABLE 2

| Line no. | The number of T0 plants analyzed | piggyBac removal from OsALS locus | | | Frequency of piggyBac removal (%) | | |
|---|---|---|---|---|---|---|---|
| | | without marker | with marker | total | without re-insertion | with re-insertion | total |
| 5 | 20 | 19 | 1 | 20 | 95.0 | 5.0 | 100.0 |
| 6 | 20 | 20 | 0 | 20 | 100.0 | 0.0 | 100.0 |
| 10 | 20 | 20 | 0 | 20 | 100.0 | 0.0 | 100.0 |
| 13 | 20 | 20 | 0 | 20 | 100.0 | 0.0 | 100.0 |
| 24 | 20 | 20 | 0 | 20 | 100.0 | 0.0 | 100.0 |
| average | | | | | 99.0 | 1.0 | 100.0 |

TABLE 3

| Line no. | The number of T0 plants analyzed | piggyBac removal from OsALS locus | | | Frequency of piggyBac removal (%) | | |
|---|---|---|---|---|---|---|---|
| | | without marker | with marker | total | without re-insertion | with re-insertion | total |
| 5 | 20 | 17 | 1 | 18 | 85.0 | 5.6 | 90.0 |
| 9 | 20 | 20 | 0 | 20 | 100.0 | 0.0 | 100.0 |
| 11 | 20 | 20 | 0 | 20 | 100.0 | 0.0 | 100.0 |
| 12 | 20 | 17 | 0 | 17 | 85.0 | 0.0 | 85.0 |
| 19 | 20 | 16 | 0 | 16 | 80.0 | 0.0 | 80.0 |
| 20 | 20 | 20 | 0 | 20 | 100.0 | 0.0 | 100.0 |
| average | | | | | 91.7 | 0.9 | 92.5 |

As a result of the marker removal analysis based on the CAPS, although unillustrated, the patterns of the detected fragments cleaved by the MfeI verified the introduction of the W548L and S627I mutations in the ALS loci of any of the GT lines A_hy and the GT lines B1_hy. Further, it was revealed that the piggyBac containing the marker gene was removed.

Moreover, as shown in Tables 2 and 3, in 90% or more of the re-differentiated plants, the MfeI-cleaved fragments were detected, indicating that the piggyBac was efficiently removed from the target ALS locus by the expression of the hyPBase (the fragments were detected from, on average, 100% of the plants in the GT lines A_hy, and 92.5% of the plants in the GT lines B1_hy).

Further, as a result of performing the PCR analysis using the primer set for specifically detecting the marker gene (hpt), only one individual in each of the GT lines A_hy and the GT lines B1_hy contained an hpt specific fragment in the MfeI-cleaved fragments by the CAPS analysis as shown in Tables 2 and 3.

As described above, it was revealed that, in 99% and 92% of the re-differentiated plants in the respective GT lines A_hy and GT lines B1_hy, the two point mutations W548L/S627I were introduced in the ALS locus via GT, while the marker gene was removed.

Test Example 2

<Verification 2 of Marker Removal from Target DNA with piggyBac>

The marker gene removal and the introduction of the W548L and S627I point mutations in the ALS locus of the T0 re-differentiated plants were analyzed by employing a direct sequencing method.

To be more specific, six individuals and 16 individuals were randomly selected from the GT lines A_hy and the GT lines B1_hy plants, respectively. Amplified fragments obtained therefrom by PCR using the primer set of ALS F1 and ALS GT-R were subjected to the direct sequencing.

The result revealed that W548L, S627I, and the silent mutation of adding the HpaI recognition site were introduced in all the analyzed plants.

Test Example 3

<Verification 3 of Marker Removal from Target DNA with piggyBac>

In order to confirm the introduction of the W548L/S627I mutations via GT and the marker gene removal by the piggyBac transposition in the ALS locus of the T0 plants, genomic DNAs were extracted from a wild type plant, a GT line A re-differentiated plant, and T0 plants of two independent lines (line nos.: 6 and 10) among the GT lines A_hy. A Southern blotting analysis was performed by the method described below.

<Southern Blotting Analysis>

Figure 5:
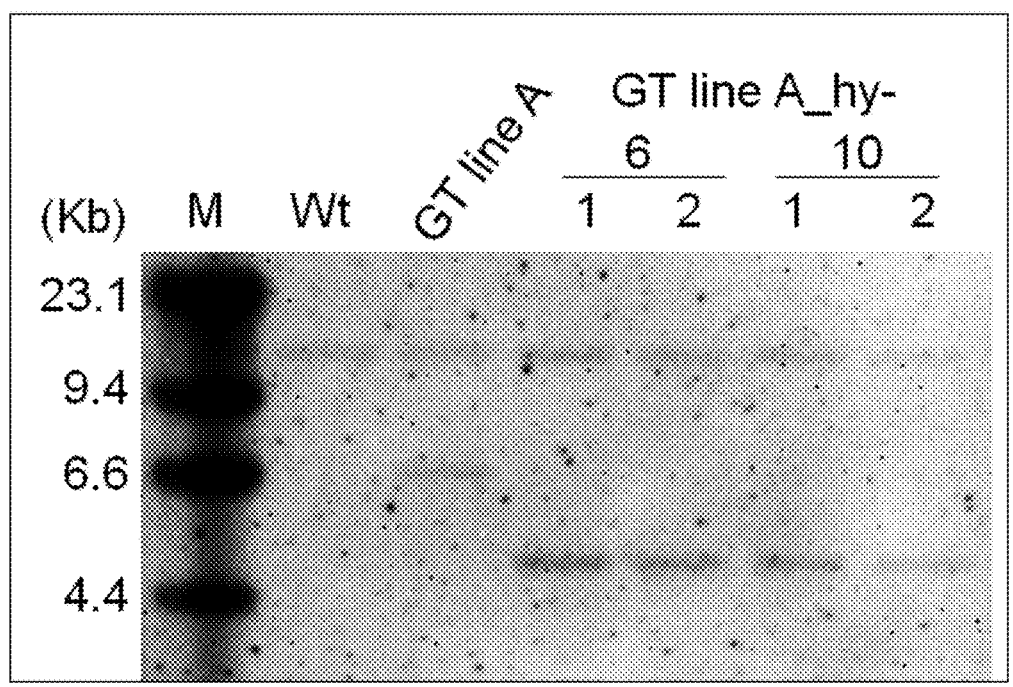
FIG. 5 is a photograph showing the result of analyzing genomic DNAs extracted from wild type rice (in the figure, "Wt"), GT vector-introduced rice (GT line A; in the figure, "GT line A", and also GT lines A constitutively expressing the piggyBac transposase (two individuals from each of GT lines A_hy: 6 and 10; in the figure, these are "GT line A_hy 6 1", "GT line A_hy 6 2", "GT line A_hy 10 1", and "GT line A_hy 10 2") by the Southern blotting method using the probe 1 shown in FIG. 4. Moreover, in the figure, "M" indicates a size marker. Note that, regarding the representations in the figure, the same shall apply to FIGS. 6 and 7 below.
Figure 6:
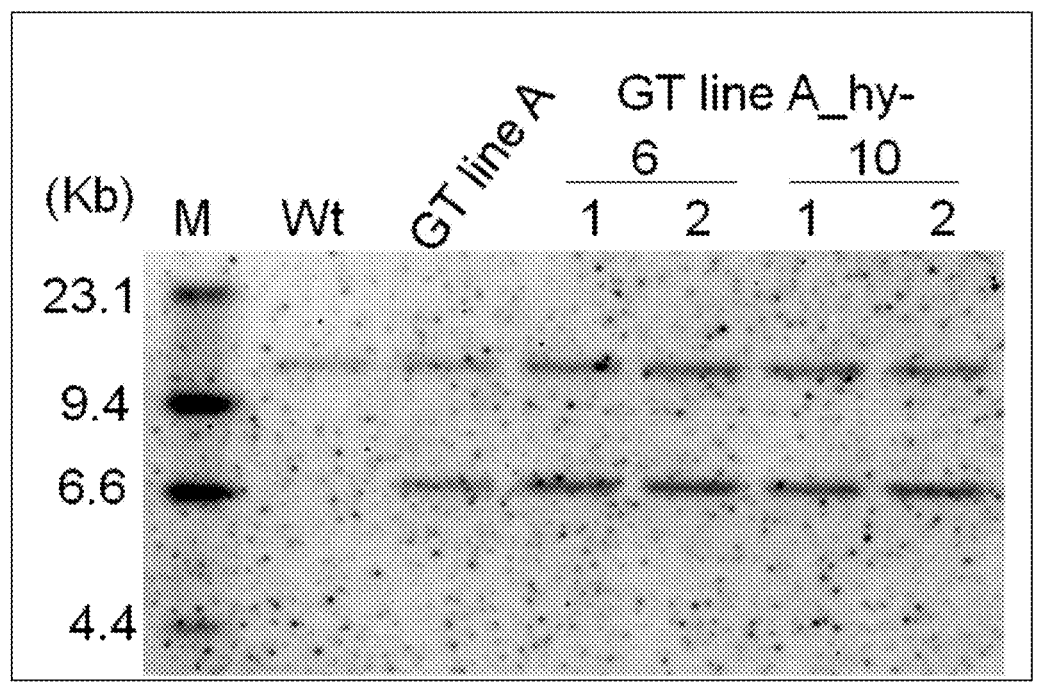
FIG. 6 is a photograph showing the result of analyzing the genomic DNAs extracted from the wild type rice, the GT line A, and the two individuals from each of GT lines A_hy: 6 and 10 by the Southern blotting method using the probe 3 shown in FIG. 4.
Figure 7:
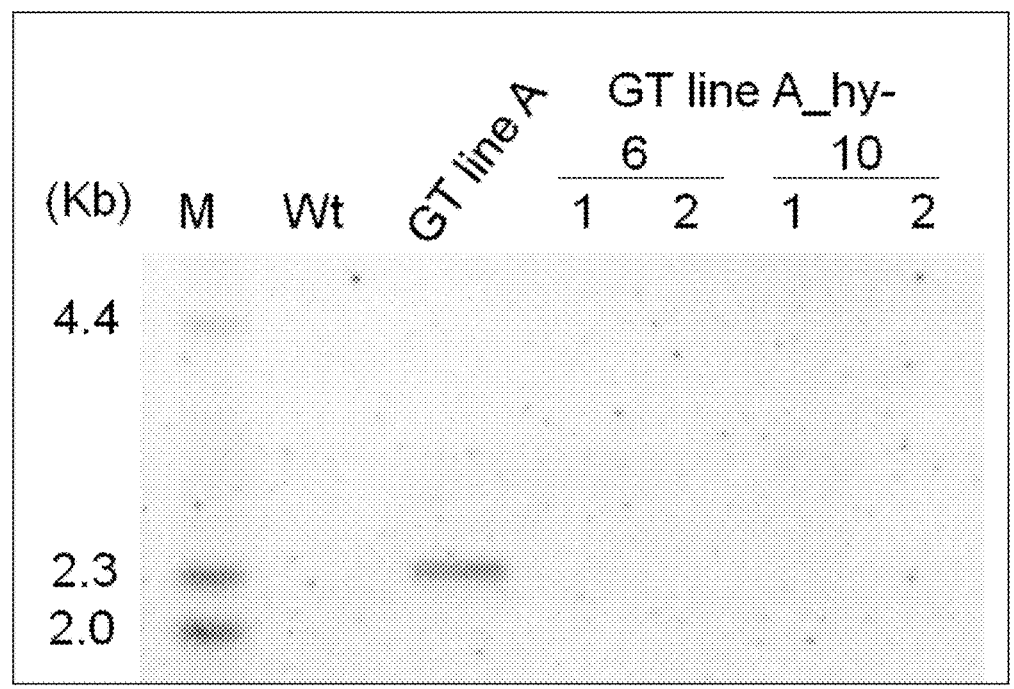
FIG. 7 is a photograph showing the result of analyzing the genomic DNAs extracted from the wild type rice, the GT line A, and the two individuals from each of GT lines A_hy: 6 and 10 by the Southern blotting method using a probe specific to the marker gene hpt.

A genomic DNA was extracted from leaves of seedlings using a Nucleon Phytopure extraction kit (manufactured by GE Healthcare) according to the attached maker protocol. Then, 2 μg of the extracted genomic DNA was treated with MfeI, and fractionated in a 1.0% agarose gel. Subsequently, the Southern blotting analysis was performed according to the digoxigenin (DIG) Application Manual (manufactured by Roche Diagnostics K. K.). FIGS. 5 to 7 show the obtained result.

Note that DNA probes specific to the ALS locus were synthesized using a PCR DIG probe synthesis kit (manufactured by Roche Diagnostics K. K.) and primers shown below, according to the attached maker protocol.

```
Probe-1
                                     (SEQ ID NO: 21)
(5'-ttcttttcaatactttcctcgcttgctct-3'
and (SEQ ID NO: 22)
5'-attcagccacttatcttgacacaaccattt-3')

Probe-2
                                     (SEQ ID NO: 23)
(5'-tgtgacagcccagtcatcat-3'
and (SEQ ID NO: 24)
5'-cgttggatcgacatcatcag-3')

Probe-3
                                     (SEQ ID NO: 25)
(5'-caaagatcgttatgtttatcggcactttg-3'
and (SEQ ID NO: 26)
5'-ctcgagctatttctttgccctc-3').
```

Figure 4:
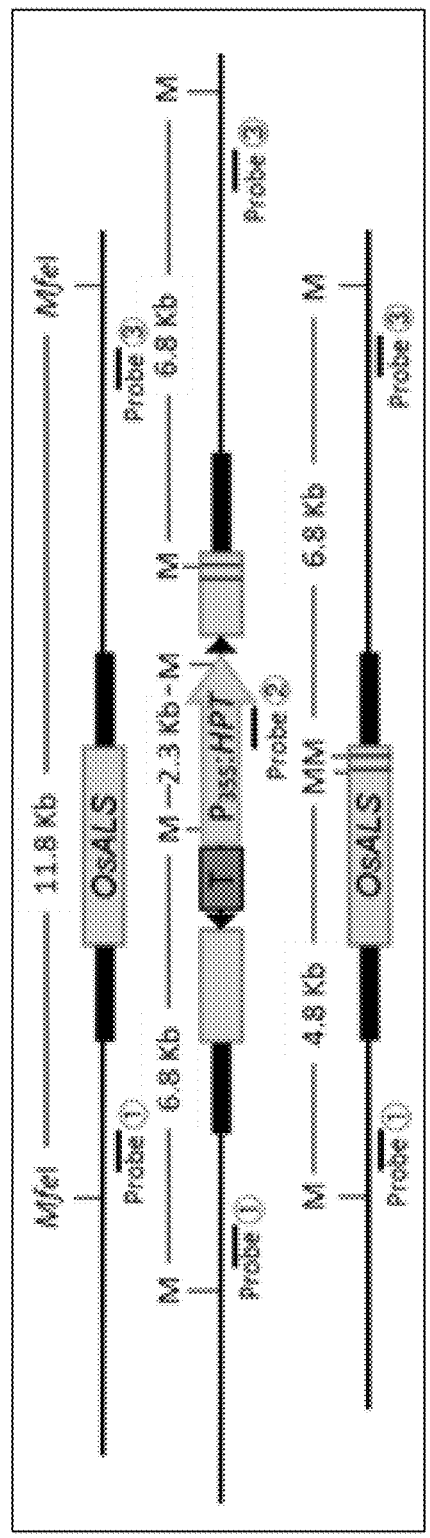
FIG. 4 is a schematic diagram showing fragments and lengths thereof expected to be detected when the rice-derived ALS locus, the GT vector, and the ALS locus containing only the desired two point mutations (W548L and S627I) introduced by homologous recombination with the vector followed by piggyBac transposon removal are analyzed by a Southern blotting method using the restriction enzyme MfeI. Moreover, the positions on the DNAs where probes 1 to 3 used in the Southern blotting analysis anneal are also shown.

Additionally, regarding the positional relation between each probe and the ALS locus, see FIG. 4.

As shown in FIG. 5, as a result of the Southern blotting analysis performed using the probe-1 on the DNAs treated with MfeI, a band (11.8-kb) derived from the wild type ALS locus and a band (6.8-kb) derived from the GT vector were detected in the GT line A re-differentiated plant.

On the other hand, as shown in FIG. 5, the bands (11.8-kb) derived from the wild type ALS locus and 4.8-kb long bands derived from the ALS locus with the piggyBac removed therefrom were detected in the GT line A_hy re-differentiated plants by the Southern blotting analysis using the probe-1.

Moreover, as shown in FIG. 6, the bands (11.8-kb) derived from the wild type ALS locus and 6.8-kb long bands derived from the ALS locus with the W548L/S627I introduced therein by GT were detected in the GT line A_hy re-differentiated plants by the Southern blotting analysis using the probe-3.

Further, as shown in FIG. 7, a 2.3-kb long band derived from the marker gene was detected only in the GT line A re-differentiated plant by the Southern blotting analysis using the hpt specific probe.

Thus, it was revealed that, in the GT line A_hy re-differentiated plants, the excised piggyBac was not re-inserted in the other genome regions.

It has been revealed that, in the piggyBac removal from a GT locus in mammalian cells described in NPL 1, the excised piggyBac is re-inserted into a different genome region from the target DNA at a frequency as high as 68 to 79%.

Moreover, as described in NPLs 2 to 5, the present inventors have revealed that although the efficiency of removing piggyBac randomly inserted in the genomic DNA of plant cells is approximately 72%, the percentage of the piggyBac and so forth removed but re-inserted is as high as 41%.

On the other hand, as apparent from the results in the above-described Test Examples 1 to 3, the present invention makes it possible to obtain a plant comprising a desired mutation introduced in a target DNA at a high frequency (92 to 99%), wherein an unnecessary sequence containing a marker gene is removed. Further, the percentage of the piggyBac excised but re-inserted is 1% and quite low. Therefore, the present invention does not need a step for removing cells having the re-insertion (negative selection or the like).

Next, in order to confirm that the above-described system including the modification of a target DNA by gene targeting (GT) and the marker removal using piggyBac without leaving any footprint was a universally utilizable technology regardless of the target gene, a rice cleistogamy 1 (Oscly1) gene was modified according to the present invention.

Note that the Oscly1 gene is a gene registered under ACCESSION No: Os04g0649100 in the Rice Annotation Project (RAP)-database (rapdb.dna.affrc.go.jp/)(regarding the function of the cly1 gene, and so forth, see the descriptions of Chen, Science, 2004, Vol. 303, pp. 2022 to 2025, and Nair et al., Proc Natl Acad Sci USA, 2010, Vol. 107, pp. 490 to 449).

On the other hand, a Cly1 gene is an orthologue of an AP2 transcription factor of *Arabidopsis thaliana* involved in the floral organ morphogenesis (see Jofuku et al., Plant Cell, 1994, Vol. 6, pp. 1211 to 1225), and has been identified as a gene responsible for cleistogamy in a barley cultivar (see supra Nair et al., 2010). Moreover, it has also been revealed that, in this cultivar, a single base substitution (single base substitution from adenine to guanine (mutation from CAGCAGCATCATCACGATTCC to CAGCAGCGTCATCACGATTCC, SEQ ID NOs: 27 and 28) occurring in a microRNA binding site produces a cleistogamous phenotype.

Thus, if the single base substitution can be introduced to the Oscly1 gene without leaving any trace, this makes it possible to provide rice having only a cleistogamous character, and consequently to obtain breeding materials also having an improved resistance to Fusarium ear blight and the like owing to the cleistogamy.

Hence, in order to confirm the effectiveness in the development of such breeding materials also, it was confirmed according to FIG. 8 and the method described below that only point mutations were allowed to remain in the end by introducing the single base substitution to the microRNA binding site of the OsCly1 gene, and then transposing the piggyBac transposon to remove the marker.

Example 3

<Construction of GT Vector>

To prepare a mutant plant having only a desired mutation in a target DNA, a DNA construct (GT vector) was constructed as follows, the DNA construct comprising a DNA homologous to the target DNA, wherein the desired mutation was introduced and a piggyBac transposon containing a marker gene was inserted in the homologous DNA.

To be more specific, first, a 6-kb genome sequence containing a coding region for the OsCly1 gene was amplified with primers 5'-ttggcgcgccttgtcgtcacgcgccagttc-3' (SEQ ID NO: 29) and 5'-ccttaattaatccagggaaatccaccactactact-3' (SEQ ID NO: 30), and inserted into an AscI/PacI site of an entry vector pENTR L1/L2. Thus, a pE(L1-L2)Oscly1 vector was prepared.

Moreover, an artificially synthesized DNA sequence was prepared in which the above-described single base substitution from adenine to guanine was introduced in a microRNA binding sequence (88 bp upstream of the stop codon) in the tenth exon of the OsCly1 gene, and further in which the sequence of the piggyBac transposon was inserted in the TTAA site of 3'-UTR of the gene.

Then, the above-described pE(L1-L2)Oscly1 and artificially synthesized DNA sequence were treated with EcoRI. Thereby, the wild type OsCly1 sequence in the vector was replaced by the OsCly1 sequence containing the single base mutation and the sequence of the piggyBac transposon introduced therein. Thus, pE(L1-L2)Oscly1pb was prepared.

Subsequently, a 4.3-kb long fragment having been treated with I-SceI was inserted into an I-SceI site inside the piggyBac transposon of the pE(L1-L2)Oscly1pb. Thus, pE(L1-L2)Oscly1pHPTb was prepared. Note that this fragment contained a rice-derived actin terminator, a cauliflower mosaic virus 35S promoter, a hygromycin phosphotransferase gene (hpt), and a rice-derived heat shock protein 17.3 terminator.

Thereafter, a 10.9-Kb sequence in the pE(L1-L2) Oscly1pHPTb was introduced into a gene targeting binary vector pKOD4 containing two DT-A expression cassettes and re-cloned by the Gateway LR Clonase II reaction. Thus, pKOD4/Oscly1pHPTb was prepared.

Example 4

Next, the GT vector (pKOD4/Oscly1pHPTb) obtained as described above was used to prepare a plant having only a desired mutation in a target DNA by the same method as that described in Example 2.

As a result, 74 independent hygromycin-tolerant calli were successfully selected from 5139 calli as shown in Table 4.

TABLE 4

| The number of calli infected with *Agrobacterium* | The number of hygromycin-tolerant calli | The number of calli having undergone homologous recombination | The number of calli in which single base substitution was introduced |
|---|---|---|---|
| 5,139 (25.6 g) | 74 | 4 | 4 |

Further, to identify transgenic calli having the GT events at the Oscly1 locus, the obtained hygromycin-tolerant calli were subjected to the following screening by PCR and sequencing analysis.

<PCR>

From a small mass of each rice callus, the genomic DNA was extracted using Agencourt Chloropure according to the attached maker protocol. Then, using the extracted genomic DNA as a template, the PCR amplification was carried out with KOD FX or KOD FX Neo and primer sets shown below (regarding the annealing positions of the Oscly1 locus and the primers, see FIG. 8).

Primer set used for Oscly1 5' side amplification:
Oscly1GT-F (5'-tcggtcggctaaggtttgctactaaaaaca-3' (SEQ ID NO: 31)) and Tact-R Primer set used for Oscly1 3' side amplification:
Thsp17.3-F and Oscly1 GT-R (5'-cttgcacgacggttctacagga-gattagtg-3' (SEQ ID NO: 32)).

Subsequently, as a result of this PCR, upstream and downstream junction fragments were detected in four independent calli as shown in Table 4. It was confirmed that, in these calli, the positive selectable marker gene was introduced in the Oscly1 locus by the homologous recombination between the GT vector and the target DNA.

<Sequencing Analysis>

Next, a 3,942-bp long fragment obtained by amplifying a 3' side of the OsCly1 gene and a 4257-bp long fragment obtained by amplifying a 3' side of the gene were introduced to a pCR-Blunt II-TOPO vector by a TOPO cloning method and cloned for the sequencing analysis.

Concretely, the universal primers M13-R and M13-F were used to confirm whether the junction sequences were as expected or not.

In addition, the insertion of the single point mutation into the microRNA target sequence in the 4257-bp long fragment was checked by the sequencing analysis using a primer Oscly1 Seq-5101F (5'-cgaccagaactcgaaccatc-3' (SEQ ID NO: 33)).

As a result of this sequencing analysis, the base substitution from adenine to guanine, that is, the mutation in the miRNA target site, was detected as shown in Table 4 in two callus lines.

Then, these two lines (cly1 GT-1 and cly1 GT-2) were subjected to the piggyBac removal treatment by the same method as for the above-described GT candidate callus lines A and B1 (Example 2). Thus, six or four lines of calli constitutively expressing the hyPBase (GT_hy calli) were selected from the callus lines (cly1 GT-1_hy-22, 23, 27, 28, 29, and 38; cly1 GT-2_hy-21, 23, 36, and 37).

Next, the GT_hy calli obtained as described above were re-differentiated by the same method as for the above-described GT lines A_hy: 5 and so on. Thus, T0 re-differentiated plants were obtained from the calli of the ten lines. From each line, 19 to 25 individuals were prepared.

Test Example 4

<Verification 4 of Marker Removal from Target DNA with piggyBac>

In order to evaluate the efficiency of removing the positive selectable marker gene via the piggyBac transposition in the T0 re-differentiated plants prepared in Example 4, the PCR analysis was carried out.

To be more specific, first, the genomic DNA was extracted from leaves of each cly1 GT-1_hy and cly1 GT-2_hy. Using the genomic DNA as a template, the PCR was carried out with PrimeSTAR GXL DNA Polymerase and a primer set (a set of Oscly1 GT-F and Tact-R, or a set of Oscly1 3' UTR-F: 5'-ggatgctattcttttgctctaccttttt-3' (SEQ ID NO: 34) and Oscly1 3' UTR-R: 5'-ttactttagtaccaacatctagaaggacga-3' (SEQ ID NO: 35)). If the piggyBac is removed from the OsCly1 GT locus by the expression of the hyPBase, a 0.6-kb long fragment is to be amplified by the primer set of Oscly1 3' UTR-F and Oscly1 3' UTR-R. On the other hand, if the piggyBac is not removed, a 5.5-kb long fragment and a 3.9-kb long fragment are to be amplified by the primer set of Oscly1 3' UTR-F and Oscly1 3' UTR-R and the primer set of Oscly1 GT-F and Tact-R, respectively.

Note that the Oscly1 3' UTR-F is a primer which anneals to 380 bp upstream of the piggyBac insertion site. The Oscly1 3' UTR-R is a primer which anneals to 223 bp downstream of the piggyBac insertion site (regarding the annealing positions of the Oscly1 locus and the primers, see FIG. 8).

Moreover, in order to analyze the frequency of the piggyBac re-inserted, the PCR analysis was carried out using the genomic DNA as a template and using PrimeSTAR GXL DNA Polymerase (manufactured by TAKARA) and the primer set for specifically detecting the marker gene: HPT-F and HPT-R. Tables 5 and 6 show the obtained result.

TABLE 5

| Line no. | The number of T0 plants analyzed | piggyBac removal from OsCly1 locus | | | Frequency of piggyBac removal (%) | | |
| --- | --- | --- | --- | --- | --- | --- | --- |
| | | without marker | with marker | total | without re-insertion | with re-insertion | total |
| 22 | 20 | 20 | 0 | 20 | 100.0 | 0.0 | 100.0 |
| 23 | 20 | 20 | 0 | 20 | 100.0 | 0.0 | 100.0 |
| 27 | 19 | 16 | 2 | 18 | 84.2 | 10.5 | 94.7 |
| 28 | 20 | 13 | 3 | 16 | 65.0 | 15.0 | 80.0 |
| 29 | 20 | 20 | 0 | 20 | 100.0 | 0.0 | 100.0 |
| 38 | 20 | 19 | 0 | 19 | 95.0 | 0.0 | 95.0 |
| average | | | | | 90.7 | 4.3 | 95.0 |

TABLE 6

| Line no. | The number of T0 plants analyzed | piggyBac removal from OsCly1 locus | | | Frequency of piggyBac removal (%) | | |
|---|---|---|---|---|---|---|---|
| | | without marker | with marker | total | without re-insertion | with re-insertion | total |
| 21 | 22 | 22 | 0 | 22 | 100.0 | 0.0 | 100.0 |
| 33 | 21 | 21 | 0 | 21 | 100.0 | 0.0 | 100.0 |
| 36 | 25 | 25 | 0 | 25 | 100.0 | 0.0 | 100.0 |
| 37 | 25 | 24 | 0 | 24 | 96.0 | 0.0 | 96.0 |
| average | | | | | 98.0 | 0.0 | 98.0 |

As shown in Tables 5 and 6, in 90% or more of the re-differentiated plants, the PCR-amplified fragments were detected, indicating that the piggyBac was removed efficiently from the target Oscly1 locus by the expression of the hyPBase (the fragments were detected from, on average, 91% of the plants in the cly1 GT-1_hy and 98% of the plants in the cly1 GT-2_hy).

As described above, it was revealed that, in 90.7% and 98% of the re-differentiated plants in the respective cly1 GT-1 and cly1 GT-2, the point mutation was introduced in the Oscly1 locus via GT, while the marker gene was removed.

Test Example 5

<Verification 5 of Marker Removal from Target DNA with piggyBac>

The marker gene removal and the introduction of the point mutation in the Oscly1 locus of the T0 re-differentiated plants were analyzed by employing a direct sequencing method.

To be more specific, ten individuals and six individuals were randomly selected from the cly1 GT-1_hy and cly1 GT-2_hy plants, respectively. PCR was performed thereon using a primer set of Oscly1-3895F (5'-ctattccctgctcgcccaat-3' (SEQ ID NO: 36)) and Oscly1 7276R (5'-agactgaaaacg-gccaatgc-3' (SEQ ID NO: 37)). Then, amplified fragments obtained therefrom were subjected to the direct sequencing using Oscly1-5101F and Oscly1-6536R (5'-cttcgagatgttaga-tatgtgtgc-3' (SEQ ID NO: 38)).

Although unillustrated, the result revealed that the single base substitution from adenine to guanine was introduced to the microRNA binding site of the OsCly1 gene in all the analyzed plants. Moreover, in the analysis of the Oscly1 gene sequence after the piggyBac transposition, the piggyBac was transposed without leaving any footprint.

Test Example 6

<Verification 6 of Marker Removal from Target DNA with piggyBac>

Figure 9:
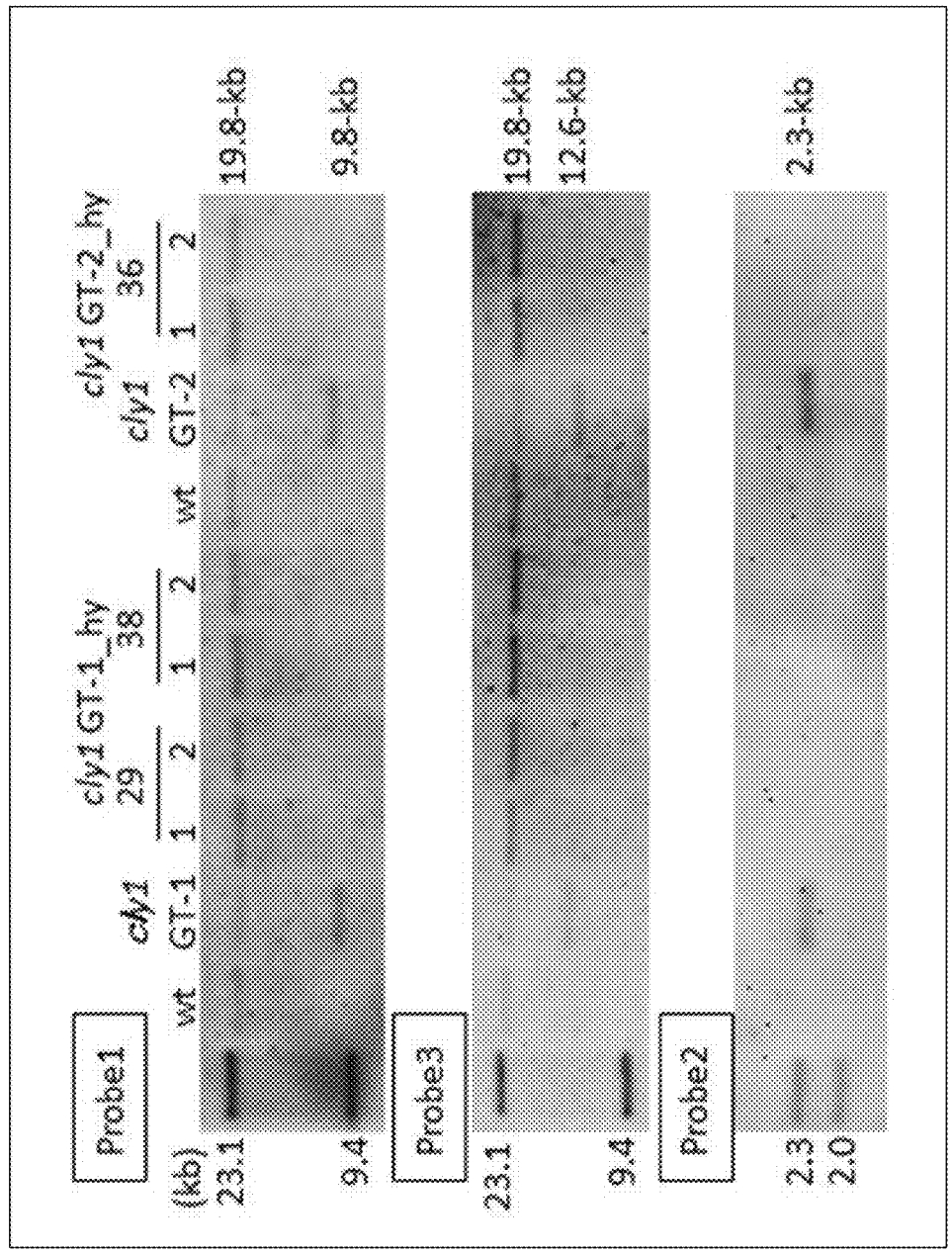
FIG. 9 is a photograph showing the result of analyzing genomic DNAs extracted from wild type rice (in the figure, "wt"), GT vector-introduced rice (in the figure, "cly1 GT-1" and "cly1 GT-2"), and also rice constitutively expressing the piggyBac transposase (in the figure, "cly1 GT-1_hy 29-1", "cly1 GT-1_hy 29-2", "cly1 GT-1_hy 38-1", "cly1GT-1_hy 38-2", "cly1GT-2_hy 36-1", and "cly1 GT-2_hy 36-2") by the Southern blotting method using the probes 1 to 3 shown in FIG. 8. Moreover, in the figure, each lane at the left end indicates a size marker.

In order to confirm the introduction of the mutation via GT and the marker gene removal by the piggyBac transposition in the Oscly1 locus of the T0 plants, genomic DNAs were extracted from wild type plants, GT line re-differentiated plants (cly1 GT-1 and cly1 GT-2), and T1 plants of two independent lines cly1 GT-1_hy (line nos: 29-1, 29-2, 38-1, 38-2) and cly1 GT-2_hy (line nos: 36-1, 36-2). A Southern blotting analysis was performed by the same method as described in Test Example 3, except that the restriction enzyme for treating the genomic DNAs was changed from MfeI to EcoRV, and that probes shown below were used. FIG. 9 shows the obtained result.

Note that DNA probes specific to the Oscly1 locus were synthesized using a PCR DIG probe synthesis kit (manufactured by Roche Diagnostics K. K.) and primers shown below, according to the attached maker protocol.

```
Probe-1
                                      (SEQ ID NO: 39)
(5'-ggttccattccctgacccggcccacct-3'
and (SEQ ID NO: 40)
5'-cagtgaatgatgcaacatgagaccgaaca-3')

Probe-2
                                      (SEQ ID NO: 23)
(5'-tgtgacagcccagtcatcat-3'
and (SEQ ID NO: 24)
5'-cgttggatcgacatcatcag-3')

Probe-3
                                      (SEQ ID NO: 41)
(5'-cagtcatctggacttgttggaattg-3'
and (SEQ ID NO: 42)
5'-catcggatgagaccacattaactt-3').
```

Figure 8:
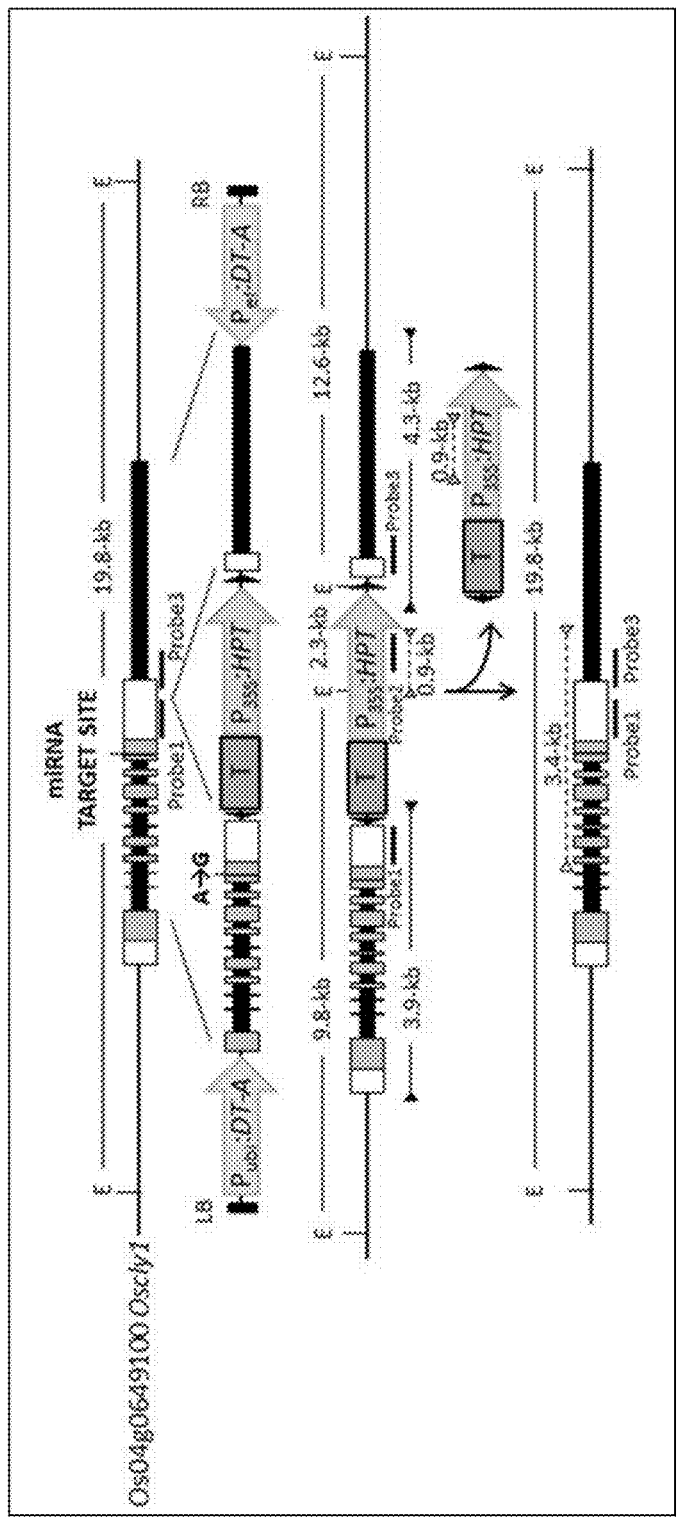
FIG. 8 is a schematic diagram showing a scheme for confirming the effectiveness of targeting a miRNA binding site (target site) in a rice-derived cleistogamy 1 gene (Oscly1) by the method for producing a plant cell comprising a mutation introduced in a target DNA of the present invention. To be more specific, the schematic diagram shows fragments and lengths thereof expected to be detected when the Oscly1 locus (the top in the figure), a GT vector (the second representation from the top in the figure), and the Oscly1 locus (the fourth representation from the top in the figure) containing a desired mutation introduced by homologous recombination with the vector (the third representation from the top in the figure) followed by piggyBac transposon removal are treated with a restriction enzyme EcoRV and analyzed by a Southern blotting method. Moreover, the positions on the DNAs where probes 1 to 3 used in the Southern blotting analysis anneal are also shown.

Additionally, regarding the positional relation between each probe and the Oscly1 locus, see FIG. 8.

As shown in FIG. 9, as a result of the Southern blotting analysis performed using the probe-1 on the DNAs treated with EcoRV, bands (19.8-kb) derived from the Oscly1 locus with no positive marker gene and bands (9.8-kb) derived from the GT vector were detected in the cly1 GT-1 and cly1 GT-2 re-differentiated plants. Moreover, as shown in FIG. 9, as a result of the Southern blotting analysis using the probe-3, the bands (19.8-kb) derived from the Oscly1 locus with no positive marker gene and bands (12.6-kb) derived from the GT vector were detected in the cly1 GT-1 and cly1 GT-2 re-differentiated plants.

On the other hand, in the cly1 GT-1_hy and cly1 GT-2_hy re-differentiated plants, only the bands (19.8-kb) derived from the wild type Oscly1 locus were detected by the Southern blotting analysis using any of the probe-1 and the probe-3.

Further, as shown in FIG. 9, 2.3-kb long bands derived from the marker gene were detected only in the cly1 GT-1 and cly1 GT-2 re-differentiated plants by the Southern blotting analysis using the hpt specific probe.

Thus, it was revealed that, in the cly1 GT-1_hy and cly1 GT-2_hy re-differentiated plants, the excised piggyBac was not re-inserted in the other genome regions.

As described above, it was confirmed that the present invention made it possible to introduce only a desired mutation in a plant cell regardless of the type of a target DNA.

INDUSTRIAL APPLICABILITY

As has been described above, the present invention makes it possible to obtain a plant cell and so forth comprising only a desired mutation introduced in a target DNA without leaving any unnecessary sequence such as a marker gene not only in the target DNA but also in regions other than the DNA.

Therefore, the method for producing a plant cell comprising a mutation introduced in a target DNA, and so forth, of the present invention are very useful in the fundamental research such as gene function analysis and in the development of breeding materials.

Sequence Listing Free Text

SEQ ID NOs: 1 to 5
<223> inverted repeat
SEQ ID NOs: 6 and 7
<223> hyperactive piggyBac transposase
SEQ ID NOs: 8 to 26 and 29 to 42
<223> Artificially synthesized primer sequence
SEQ ID NOs: 27 and 28
<223> micro RNA targeting site

The invention claimed is:

1. A method for producing a plant cell comprising a mutation introduced in a target DNA, the method comprising the following steps (i) to (iii):
   (i) a step of introducing into plant cells a DNA construct comprising a DNA homologous to a target DNA, wherein a desired mutation is introduced and a piggyBac transposon containing a marker gene is inserted in the homologous DNA; and
   (ii) a step of selecting a plant cell, in which the mutation and the piggyBac transposon are introduced in the target DNA via homologous recombination, based on an expression of the marker gene; and
   (iii) a step of removing the piggyBac transposon from the target DNA by constitutively expressing a piggyBac transposase in the cell selected in the step (ii).

2. The method according to claim 1, wherein the marker gene contained in the piggyBac transposon is a positive selectable marker gene or a reporter gene,
   the positive selectable marker gene encodes a protein essential for the growth of the plant cell or a protein for promoting the growth,
   negative selectable marker genes are added respectively to both ends of the DNA homologous to the target DNA, and
   the negative selectable marker gene encodes a protein for inhibiting the growth or a protein for suppressing the growth.

* * * * *